(12) United States Patent
Naigertsik et al.

(10) Patent No.: US 11,933,680 B2
(45) Date of Patent: Mar. 19, 2024

(54) SYSTEM AND METHOD FOR DETECTING A MODIFICATION OF A COMPOUND DURING A TRANSIENT PERIOD

(71) Applicant: GREENVIBE WN SENSING TECHNOLOGIES LTD., Beer Sheva (IL)

(72) Inventors: Oleg Naigertsik, Haifa (IL); Orit Harel, Haifa (IL); Shlomi Turgeman, Haifa (IL); Tomer Froimovich, Haifa (IL)

(73) Assignee: GREENVIBE WN SENSING TECHNOLOGIES LTD., Beer Sheva (IL)

( * ) Notice: Subject to any disclaimer, the term of this patent is extended or adjusted under 35 U.S.C. 154(b) by 535 days.

(21) Appl. No.: 16/769,915

(22) PCT Filed: Dec. 4, 2018

(86) PCT No.: PCT/IL2018/051329
§ 371 (c)(1),
(2) Date: Jun. 4, 2020

(87) PCT Pub. No.: WO2019/111252
PCT Pub. Date: Jun. 13, 2019

(65) Prior Publication Data
US 2021/0131883 A1    May 6, 2021

(30) Foreign Application Priority Data

Dec. 4, 2017    (IL) .......................................... 256108

(51) Int. Cl.
*G01L 1/12*    (2006.01)
*A61M 5/50*    (2006.01)
(Continued)

(52) U.S. Cl.
CPC .............. *G01L 1/125* (2013.01); *G01L 1/241* (2013.01); *G01N 3/08* (2013.01); *G01N 29/043* (2013.01);
(Continued)

(58) Field of Classification Search
CPC ........... G01L 1/125; G01L 1/241; G01N 3/08; G01N 29/043; G01N 29/223;
(Continued)

(56) References Cited

U.S. PATENT DOCUMENTS 4,763,927 A    8/1988 Schneider
4,766,516 A    8/1988 Ozdemir et al.
(Continued)

FOREIGN PATENT DOCUMENTS

CN        2401940      10/2000
CN       101735614      6/2010
(Continued)

OTHER PUBLICATIONS

Chenglu Jin et al., "Secure and Efficient Initialization and Authentication Protocols for Shield"; University of Connecticut, Jun. 27, 2015, pp. 1-24.
(Continued)

*Primary Examiner* — Jonathan M Dunlap
(74) *Attorney, Agent, or Firm* — PEARL COHEN ZEDEK LATZER BARATZ LLP

(57) ABSTRACT

A method and an apparatus for detecting a modification of a compound, the modification occurring during a transient period. The method may include: coupling at least one substance portion comprising ferro elastic material to a compound, the substance portion being configured to change a polarization level thereof continuously in response to a strain gradient applied thereto over the a transient period which results in said modification; sensing a physical prop-
(Continued)

erty of said substance portion affected by the polarization level of the substance portion, due to the modification; and determining, using a computer processor, the modification, based on the sensed physical property of the substance portion.

18 Claims, 18 Drawing Sheets

(51) Int. Cl.
| | |
|---|---|
| G01L 1/24 | (2006.01) |
| G01N 3/08 | (2006.01) |
| G01N 29/04 | (2006.01) |
| G01N 29/07 | (2006.01) |
| G01N 29/22 | (2006.01) |
| G01N 29/44 | (2006.01) |
| G01N 33/38 | (2006.01) |
| G06K 19/073 | (2006.01) |
| G07D 7/2033 | (2016.01) |
| H04B 11/00 | (2006.01) |
| H10N 30/30 | (2023.01) |
| H10N 30/857 | (2023.01) |

(52) U.S. Cl.
CPC ........... *G01N 29/07* (2013.01); *G01N 29/223* (2013.01); *G01N 33/383* (2013.01); *H04B 11/00* (2013.01); *H10N 30/302* (2023.02); *H10N 30/857* (2023.02); *A61M 5/5086* (2013.01); *G01N 29/04* (2013.01); *G01N 29/4409* (2013.01); *G01N 2203/0092* (2013.01); *G01N 2291/025* (2013.01); *G01N 2291/0251* (2013.01); *G06K 19/07372* (2013.01); *G07D 7/2033* (2013.01)

(58) Field of Classification Search
CPC ....... G01N 33/383; G01N 2291/02582; G01N 2291/025; G01N 29/07; G01N 29/4409; G01N 29/04; G01N 2203/0092; G01N 2291/0251; H01L 41/1132; H01L 41/193; H04B 11/00; G07D 7/2033; A61M 5/5086; G06K 19/07372; H10N 30/302; H10N 30/857
See application file for complete search history.

(56) References Cited

U.S. PATENT DOCUMENTS

| | | | |
|---|---|---|---|
| 4,792,667 | A | 12/1988 | Chen |
| 6,848,049 | B1 | 1/2005 | Tailliet |
| 8,516,269 | B1 | 8/2013 | Hamlet et al. |
| 9,230,050 | B1 | 1/2016 | Lanzerotti |
| 9,515,157 | B2 | 12/2016 | Woerdenweber |
| 2003/0054158 | A1 | 3/2003 | Smith et al. |
| 2003/0194578 | A1 | 10/2003 | Tam et al. |
| 2003/0204743 | A1 | 10/2003 | Devadas et al. |
| 2008/0002882 | A1 | 1/2008 | Voloshynovskyy et al. |
| 2008/0169833 | A1 | 7/2008 | Anderson et al. |
| 2008/0282209 | A1 | 11/2008 | Anderson et al. |
| 2008/0303376 | A1 | 12/2008 | Jakli et al. |
| 2009/0100392 | A1 | 4/2009 | Ivaldi |
| 2009/0306920 | A1 | 12/2009 | Zwinger et al. |
| 2010/0213951 | A1 | 8/2010 | Lewis |
| 2010/0237854 | A1 | 9/2010 | Kumhyr et al. |
| 2010/0241864 | A1 | 9/2010 | Kelley et al. |
| 2011/0148457 | A1 | 6/2011 | Abramovici |
| 2011/0264921 | A1 | 10/2011 | Keil |
| 2012/0051389 | A1 | 3/2012 | Marc et al. |
| 2012/0179812 | A1 | 7/2012 | Keller, III |
| 2012/0212253 | A1 | 8/2012 | Lewis |
| 2012/0223403 | A1 | 9/2012 | Keller, III et al. |
| 2012/0317662 | A1 | 12/2012 | Neo et al. |
| 2013/0127442 | A1 | 5/2013 | Satoh et al. |
| 2013/0141137 | A1 | 6/2013 | Krutzik et al. |
| 2013/0147511 | A1 | 6/2013 | Koeberl et al. |
| 2013/0222109 | A1 | 8/2013 | Lim |
| 2013/0276059 | A1 | 10/2013 | Lewis et al. |
| 2013/0318607 | A1 | 11/2013 | Reed et al. |
| 2014/0100807 | A1 | 4/2014 | Rosenblatt et al. |
| 2014/0103344 | A1 | 4/2014 | Tehranipoor et al. |
| 2014/0252487 | A1 | 9/2014 | Stephens et al. |
| 2014/0253222 | A1 | 9/2014 | Merchant et al. |
| 2014/0258156 | A1 | 9/2014 | Tziazas et al. |
| 2014/0271365 | A1 | 9/2014 | Pathak et al. |
| 2015/0078518 | A1 | 3/2015 | Tziazas et al. |
| 2015/0130506 | A1 | 5/2015 | Bhunia et al. |
| 2015/0137830 | A1 | 5/2015 | Keller, III et al. |
| 2015/0207627 | A1 | 7/2015 | Yamamoto et al. |
| 2015/0219714 | A1 | 8/2015 | Hamilton et al. |
| 2015/0247892 | A1 | 9/2015 | Robertazzi et al. |
| 2015/0260786 | A1 | 9/2015 | Hampel et al. |
| 2015/0269592 | A1 | 9/2015 | Hieftje et al. |
| 2015/0301109 | A1 | 10/2015 | O'Flynn |
| 2015/0358337 | A1 | 12/2015 | Keller |
| 2016/0047855 | A1 | 2/2016 | Bhunia et al. |
| 2016/0047932 | A1 | 2/2016 | Akaba et al. |
| 2016/0072632 | A1 | 3/2016 | Blanton |
| 2016/0080153 | A1 | 3/2016 | Suzuki |
| 2016/0103065 | A1 | 4/2016 | Lee et al. |
| 2016/0124041 | A1 | 5/2016 | Pathak et al. |
| 2021/0131883 | A1 | 5/2021 | Naigertsik et al. |
| 2021/0140924 | A1 | 5/2021 | Weiss et al. |

FOREIGN PATENT DOCUMENTS

| | | |
|---|---|---|
| CN | 101909408 | 12/2010 |
| CN | 101944194 | 1/2011 |
| CN | 102147875 | 8/2011 |
| CN | 201993789 U | 9/2011 |
| CN | 102306318 | 1/2012 |
| CN | 102436619 | 5/2012 |
| CN | 102467677 | 5/2012 |
| CN | 104101792 | 10/2014 |
| CN | 105218087 | 1/2016 |
| CN | 104457964 | 7/2017 |
| CN | 108196188 | 6/2018 |
| EP | 1020813 | 7/2000 |
| EP | 2950233 | 12/2015 |
| EP | 3721205 | 8/2021 |
| GB | 2460071 | 11/2009 |
| IL | 133460 | 10/2003 |
| IL | 256108 | 6/2019 |
| IN | 201641024214 | 1/2018 |
| JP | 2000-276627 | 10/2000 |
| WO | WO 0017826 | 3/2000 |
| WO | WO 2010/105993 | 9/2010 |
| WO | WO 2014/075617 | 5/2014 |
| WO | WO 2015/081163 | 6/2015 |
| WO | WO 2015/089346 | 6/2015 |
| WO | WO 2015/140731 | 9/2015 |
| WO | WO 2019/111252 | 6/2019 |
| WO | WO 2022/153317 | 7/2022 |

OTHER PUBLICATIONS

Steve H. Weingart, "Physical Security Devices for Computer Subsystems: A Survey of Attacks and Defenses", Secure Systems and Smart Card Group IBM, Thomas J. Watson Research Center, Hawthorne, NY; CHES 2000, LNCS 1965, pp. 302-317, 2000.

Broad Agency Announcement, Supply Chain Hardware Integrity for Electronics Defense (SHIELD), Microsystems Technology Office, DARPA-BAA-14-16, Mar. 3, 2014, pp. 3-54.

Defense Advanced Research Projects Agency, Microsystems Technology Office, Special Notice, Shield Proposers' Day, DARPA-SN-14-22, Feb. 2014.

Statement by Arati Prabhakar, Director, Defense Advanced Research Projects Agency (DARPA) Before the Subcommittee on Emerging Threats and Capabilities, Armed Services Committee, U.S. House

(56) References Cited

OTHER PUBLICATIONS of Representatives; Department of Defense Fiscal Year 2017 Science and Technology Programs: Defense Innovation to Create the Future Military Force, Feb. 24, 2016, pp. 1-23.
Davood Shahrjerdi et al., "Shielding and Securing Integrated Circuits with Sensors"; 2014 IEEE: pp. 170-174.
Joe Grand, "Practical Secure Hardware Design for Embedded SYstems", Grand Idea Studio, Inc., this paper was originally published by CMP Media in the Proceedings of the 2004 Embedded Systems Conference, San Francisco, California, Mar. 29-Apr. 1, 2004; Last updated on Jun. 23, 2004.
"Winning the Battle Against Counterfeit Semiconductor Products", A report of the SIA Anti-Counterfeiting Task Force, Aug. 2013, pp. 1-27.
International Search Report for PCT Application No. PCT/IL2018/051329, dated Mar. 5, 2019.
Office Action for Israel Patent Application No. 133460, dated Oct. 30, 2019.

Huang Wenbin et al.: "Cracks monitoring and characterization using BaSrTiOflexoelectric strain gradient sensors", Proceedings of SPIE, IEEE, US, vol. 9061, Mar. 8, 2014, pp. 906119-906119.
Shun-Di Hu et al.: "Signal analysis of flexoelectric transducers on rings", Piezoelectricity, Acoustic Waves and Device Applications (SPAWDA), 2010 Symposium On, IEEE, Dec. 10, 2010, pp. 106-111.
Rey Alejandro D. et al.: "Stress-Sensor Device Based on Flexoelectric Liquid Crystalline Membranes", CHEMPHYSCHEM—A European Journal of Chemical Physics & PhysicalChemistry., vol. 15, No. 7, Oct. 2, 2013, pp. 1405-1412.
Hodnett M, Chow R, Zeqiri B, High-frequency acoustic emissions generated by a 20 KHz sonochemical horn processor detected using a novel broadband acoustic sensor: a preliminary study. Ultrasonics sonochemistry. Vol. 11, No. 6, pp. 441-454. Sep. 1, 2004.
Shah H, Balasubramaniam K, Rajagopal p. In-situ process-and online structural health-monitoring of composites using embedded acoustic waveguide sensors. Journal of Physics Communications. Vol. 1, No. 5, p. 055004. Dec. 7, 2022.

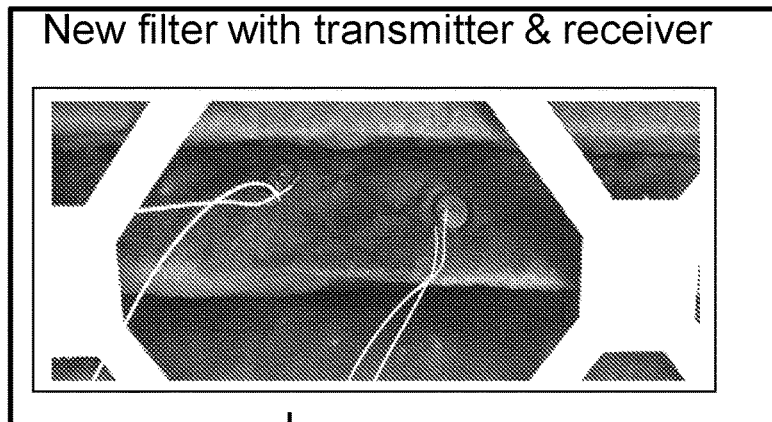
Figure 14A
Figure 14B
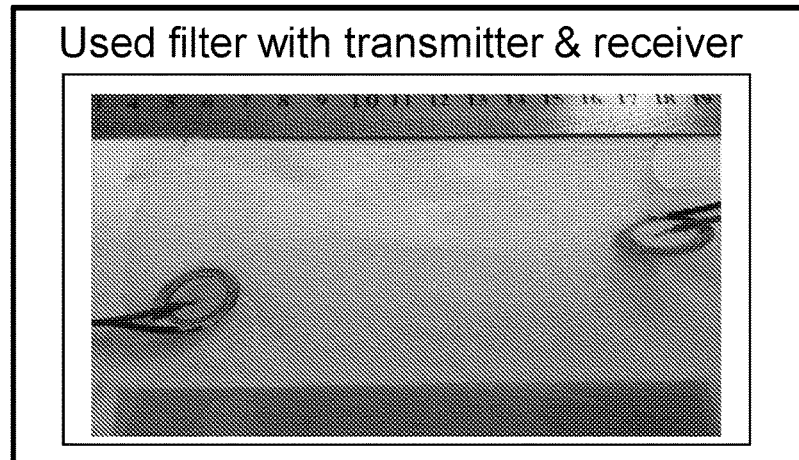
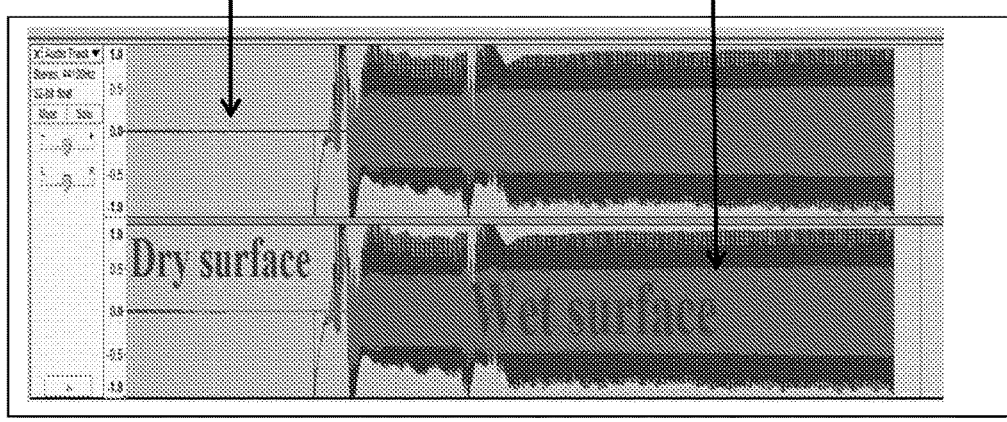
Dry/New vs. Wet/Used signal Figure 14C

SYSTEM AND METHOD FOR DETECTING A MODIFICATION OF A COMPOUND DURING A TRANSIENT PERIOD

CROSS-REFERENCE TO RELATED APPLICATIONS

This application is a National Phase Application of PCT International Application No. PCT/IL2018/051329, International Filing Date Dec. 4, 2018, entitled: "SYSTEM AND METHOD FOR DETECTING A MODIFICATION OF A COMPOUND DURING A TRANSIENT PERIOD", published on Jun. 13, 2019, under PCT International Application Publication No. WO 2019/111252, which claims the priority of Israel Patent Application No. 256108, filed on Dec. 4, 2017, which is hereby incorporated by reference in its entirety.

FIELD OF THE INVENTION

The present invention relates generally to the field of sensing modification in compounds.

BACKGROUND OF THE INVENTION

Prior to the background of the invention being set forth, it may be helpful to provide definitions of certain terms that will be used hereinafter.

The term "piezo-electric material" as used herein is defined as any material that is associated with the piezo-electricity phenomena. Piezo-electricity being defined as electric charge that accumulates in certain solid materials (such as crystals and certain ceramics) in response to applied mechanical stress. Ceramics with randomly oriented grains must be ferroelectric to exhibit piezo-electricity. The macroscopic piezo-electricity is possible in textured polycrystalline non-ferroelectric piezo-electric materials, Lead Zirconate Titanate, more commonly known as PZT is the most common piezo-electric ceramic in use today.

The term "poled" and "un-poled" substance as used herein relate to the polarization of piezo-electric material which is a metric that may easily be calculated for crystals by summing up the dipole moments per volume of the crystallographic unit cell. As every dipole is a vector, the dipole density P is a vector field. Dipoles near each other tend to be aligned in regions called Weiss domains. The domains are usually randomly oriented, but can be aligned using the process of poling (not the same as magnetic poling), a process by which a strong electric field is applied across the material, usually at elevated temperatures. Different partially poled states of the substance may be introduced between the poled and un-poled states.

The term "ferro-elastic" as used herein is defined as a material able to exhibit a spontaneous strain. When stress is applied to a ferro-elastic material, a phase change will occur in the material from one phase to an equally stable phase, either of different crystal structure (e.g. cubic to tetragonal), or of different orientation (a 'twin' phase). This stress-induced phase change results in a strain gradient in the material. The pressure applied to the ferro-elastic material may generate a pressure-induced polarization or partial polarization, which exists as long as the strain gradient is maintained. In accordance with an alternative definition "flexoelectricity" being the property of "ferro-elastic" material is the response of the dielectric polarization to a macroscopic strain gradient.

The term "Curie temperature" (TC) as used herein is defined as the temperature at which certain materials lose a specific property. In the context of this application Curie temperature is used to describe the phase transition between poled and un-poled piezo-electric material. The order parameter in this case is the electric polarization that goes from a finite value to near zero when the temperature is increased above the Curie temperature.

The wide spread phenomena of counterfeit of different articles of manufacture in almost any retail domain causes on one hand an economy loss for many manufacturers and on the other hand generates poor and unreliable products for the customers.

Yet another phenomenon is the unauthorized reuse of authentic products, where products such as electronic components are being taken from a stripped-off system and reused in another system. This may pose not only an economic issue but also safety issues where the average time before failure is not accurate anymore as the product has been already used for some time.

In the case of reused or fake integrated circuits (IC) this may even cause a serious risk for many different systems such as aircrafts, unmanned aerial vehicle (UAV), tanks, medical equipment and others, as fake/reused IC's are prone to low performance and malfunctioning in a higher probability.

Therefore, there is a need to be able to monitor the authenticity and usage conditions of some article of manufacture.

Some of the challenges to address in such a monitoring ability may include price of the process, the ability to monitor the authenticity/usage easily in real time, making it difficult to tamper with the monitoring ability post manufacturing, not overly interfering with the original manufacturing process, ability to adjust the monitoring ability and tailoring it for accuracy and various other parameters concerning usage and authenticity.

The discussion above is presented as a general overview of related art in this field and should not be construed as an admission that any of the information it contains constitutes prior art against embodiments of present patent application discussed hereinafter.

BRIEF SUMMARY OF THE INVENTION

Some embodiments of the present invention suggest an apparatus for detecting usage condition and additionally or alternatively, the authenticity of an article of manufacture.

The apparatus may comprise a ferro-elastic substance that may be physically coupled to an article of manufacture and responsive to a change in the usage condition of the article of manufacture and may undergo a change in a physical property, furthermore the change in the physical property of the monitoring substance may be indicative of the level of usage and may indicate a first usage of the article. Alternatively, it can be indicative of the qualitative and quantitative indicators of the usage of the article of manufacture.

According to some embodiments of the present invention, the substance undergoes a change in at least one physical property from a first phase to a second phase when said article of manufacture is affected by said usage condition.

According to some embodiments of the present invention, the substance may be contained within the article of manufacture.

According to some embodiments of the present invention, said ferro-elastic substance undergoes structural phase transition.

According to some embodiments of the present invention, the article may include at least two substances, wherein at least two substances are a set of Ferro-elastic and piezoelectric substance.

According to some embodiments of the present invention, the change in at least one physical property may be predicted for known environmental conditions such as temperature and humidity using a historical database that exists in the system.

According to some embodiments of the present invention, a higher level of accuracy in predicting the change in at least one physical property may be obtained by using a local sensing element to detect local weather conditions over a short time period; this improved forecast may be carried out in a remote server where an algorithm uses the sensor data and local weather forecast, via the site system embedded GPS, combining the two, using a look-up table.

According to some embodiments of the present invention, the apparatus may be configured to transmit data for an extended period of time, powered by a rechargeable power supply.

Some embodiments may include a plurality of sensors, connected together within an article of manufacture, with a main sensor from which a power socket will lead out externally for connection to a power supply for charging all the sensors.

Some embodiments may further include a power transition line connected the main sensor to the structural power supply.

Some embodiments may further include sensors located close enough to a wireless recharge device to enable energy transfer through radio frequency electromagnetic waves.

Some embodiments may further include a power distribution unit comprising a battery which may be able to be charged using radio frequency electromagnetic waves.

According to some embodiments of the present invention, the apparatus may include a main sensor module which may comprise a central processing unit and a data transmission module; further sensing modules may comprise a temperature meter and simple circuit, furthermore the data may be transmitted through a wired connection to the main sensor module or via a wireless communication protocol to the main hub.

Some embodiments may further include one or more secondary hubs that receive data from sensors and transmit and to the main hub, wherein the main hub transmits the data to the internet, wherein the data transfer is achieved via at least one of: 3G communication, autonomous vehicle linkage and satellite communication.

Some other embodiments provide a system for detecting usage condition of an article of manufacture. The system may include: a ferro-elastic substance, physically coupled to said article of manufacture and configured to undergo a change in at least one physical property thereof, responsive to a change in said at least one of: the manufacturing process and the usage condition of said article of manufacture, wherein said change in the at least one physical property is irreversible, and wherein said change in usage condition comprises at least a first usage of said article of manufacture post manufacturing thereof; and at least one detector configured to sense said change in the at least one physical property of said substance.

According to some embodiments of the present invention, the compound may consist of glue or concrete, and may further comprise a ferro-elastic portion. Over the duration of the transient period, the compound may be subject to numerous stresses and strains due to changing external, environmental conditions.

The ferro elastic portion of the compound may take on these forces and may further retain the history of said forces that it underwent over the transient period. In examining the forces that the ferro-elastic portion underwent, a more general picture and awareness of the changes that the compound goes through may be ascertained.

Namely, in analyzing the change in polarization of the ferro-elastic material, a property whose changes are indicative of the overall effects on the compound. The polarization changes may be detected via sensors and a look-up table may be consulted to determine the exact nature of the detected changes and thus the larger implications for the compound in which the ferro-elastic material resided during the transient period.

According to some embodiments of the present invention, the system may further include an in-situ presence indicator for detecting the presence of pedestrians or vehicles in the vicinity of the detector, configured to take account of excess strain Some other embodiments of the invention may provide a system including a door traffic counter in a predefined place within the vicinity of the detector, configured to take account of excess strain.

Some other embodiments provide a method for detecting at least one of: a usage condition and a manufacturing process of an article of manufacture, the method may include: physically coupling a substance, to said article of manufacture and configured to undergo a change in at least one physical property thereof, responsive to a change in said at least one of: the manufacturing process and the usage condition of said article of manufacture; and sensing said change in the at least one physical property of said substance, wherein said change in the at least one physical property is irreversible, and wherein said change in usage condition comprises at least a first usage of said article of manufacture post manufacturing thereof.

According to some embodiments of the present invention, an array of sensors may be distributed in predefined places to provide relevant information regarding the structure, known as Structure Health Monitoring (SHM). The sensors may be calibrated to provide more accurate readings of ferro-elastic behavior; if offset occurs, this may be cancelled out by software manipulation.

According to some embodiments of the present invention, the physically coupling is carried out at a specific point of time based on physical properties of at least one of: the usage condition and the manufacturing process of an article of manufacture.

These additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding substances or sections. In the accompanying drawings:

FIG. 14A-C show experiment results illustrating non-limiting example of the monitoring substance properties according to some embodiments of the present invention;

DETAILED DESCRIPTION OF THE INVENTION

Figure 1:
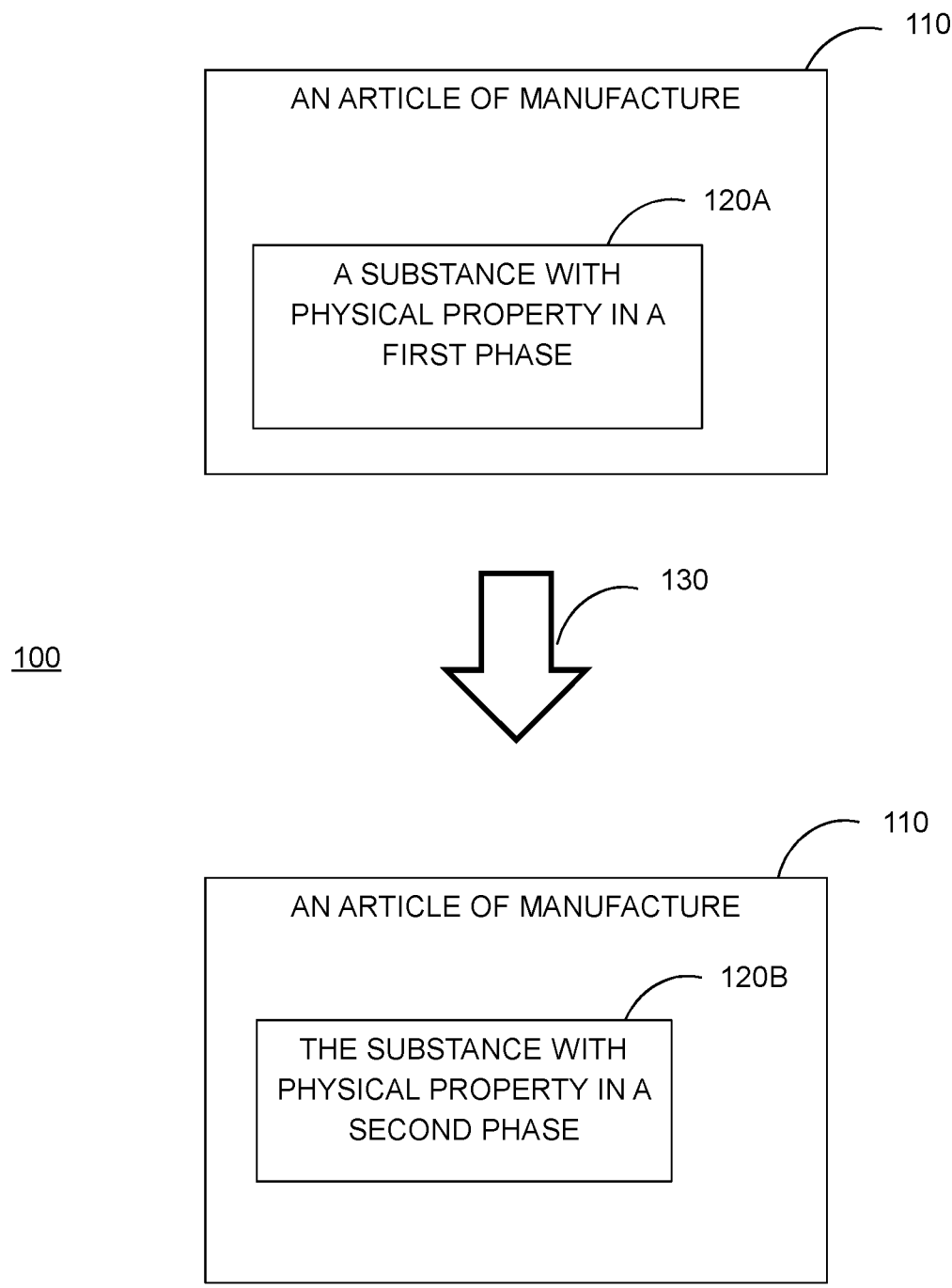
FIG. 1 is a block diagram illustrating an aspect of a monitoring substance implemented in an article of manufacture, according to some embodiments.

With specific reference now to the drawings in detail, it is stressed that the particulars shown are for the purpose of example and solely for discussing the preferred embodiments of the present invention and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before explaining the embodiments of the invention in detail, it is to be understood that the invention is not limited in its application to the details of construction and the arrangement of the components set forth in the following descriptions or illustrated in the drawings. The invention is applicable to other embodiments and may be practiced or carried out in various ways. Also, it is to be understood that the phraseology and terminology employed herein is for the purpose of description and should not be regarded as limiting.

FIG. 1 is a block diagram illustrating an aspect of a monitoring substance 120A, 120B implemented on an article of manufacture 110, according to some embodiments of the present invention. In a process 100, an article of manufacture 110 (broadly defined as any item produced in a process of manufacturing) has a substance 120A, 120B, physically coupled thereto and configured to undergo a change in at least one physical property thereof (specifically from 120A to 120B), responsive to a change in a usage condition 130 of article of manufacture 110.

According to some embodiment of the present invention, the piezo-electric material used as monitoring substance is lead free Restriction of Hazardous Substances Directive (RoHS) European Waste Electrical and Electronic Equipment Directive (WEEE) compliance.

According to some embodiments of the present invention, the change in the at least one physical property (i.e. from 120A to 120B) is irreversible or can be controlled, or at least only reversible using specific and dedicated lab equipment which are not readily available. More specifically, the change in usage condition 130 include a first ever usage of article of manufacture 110 post manufacturing process (i.e.—first use by a consumer). It should be noted that usage may be the first usage of an end user post manufacturing process.

Figure 2:
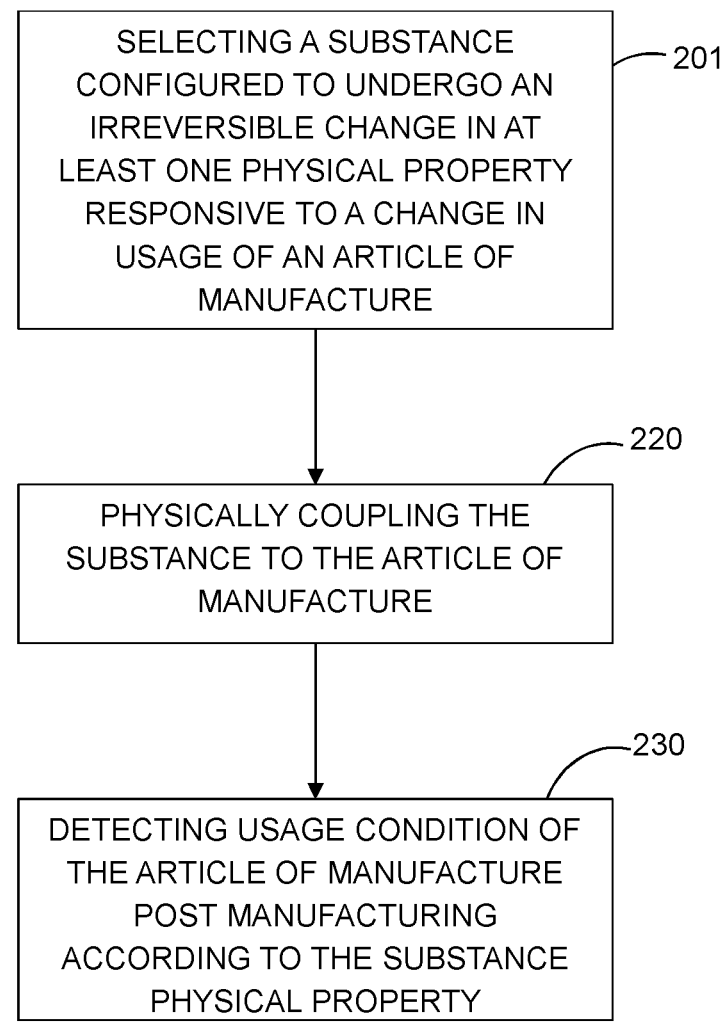
FIG. 2 shows a flowchart diagram of a method using a substance for monitoring a usage condition of an article of manufacture according to some embodiments.

FIG. 2 shows a high-level flowchart diagram of a generalized method 200 using a substance for monitoring a usage condition of an article of manufacture according to some embodiments of the present invention. Method 200 may include the following step: selecting a substance configured to undergo a predefined change of at least one physical property responsive to a change in usage of an article of manufacture 210; physically coupling the substance to the article of manufacture 220; and detecting usage condition of the article of manufacture post manufacturing according to the substance physical property 230.

Figure 3:
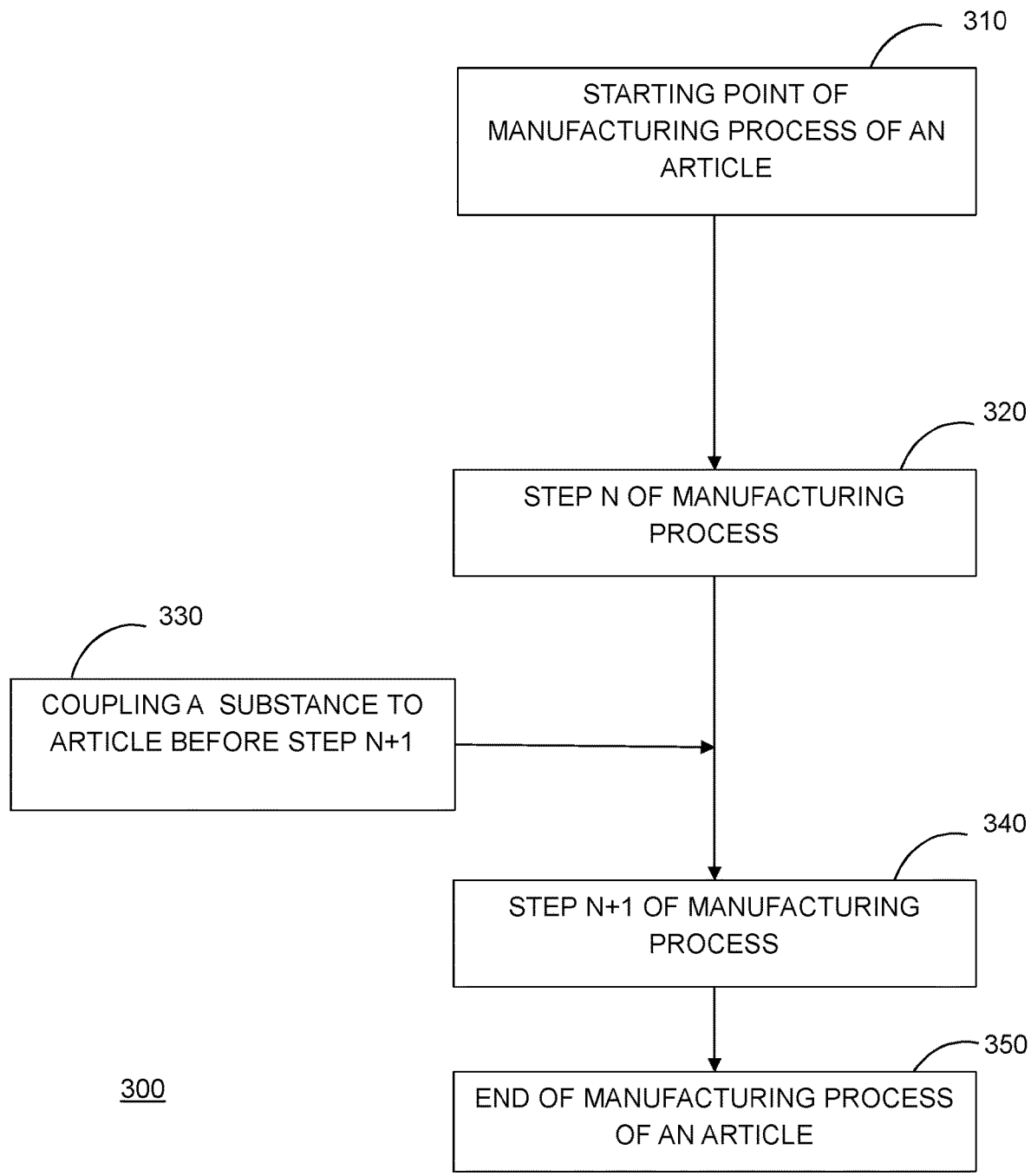
FIG. 3 shows a schematic block diagram illustrating manufacturing process according to some embodiments of the invention.

FIG. 3 shows a schematic block diagram illustrating a manufacturing process according to some embodiments of the invention. Any standard manufacturing process may be illustrated by process 300 which may include starting point of manufacturing process of an article 310; step N of manufacturing process 320. Then, in accordance with some embodiments of the present invention, a step of coupling a substance to article before step N+1 330 is being inserted without interfering with process 300 which then proceeds to step N+1 of manufacturing process 340. Finally, the end of manufacturing process of an article is reached 350 and any usage or change to the article of manufacture is regarded as post manufacture change that may affect the substance coupled in step 320.

Figure 4:
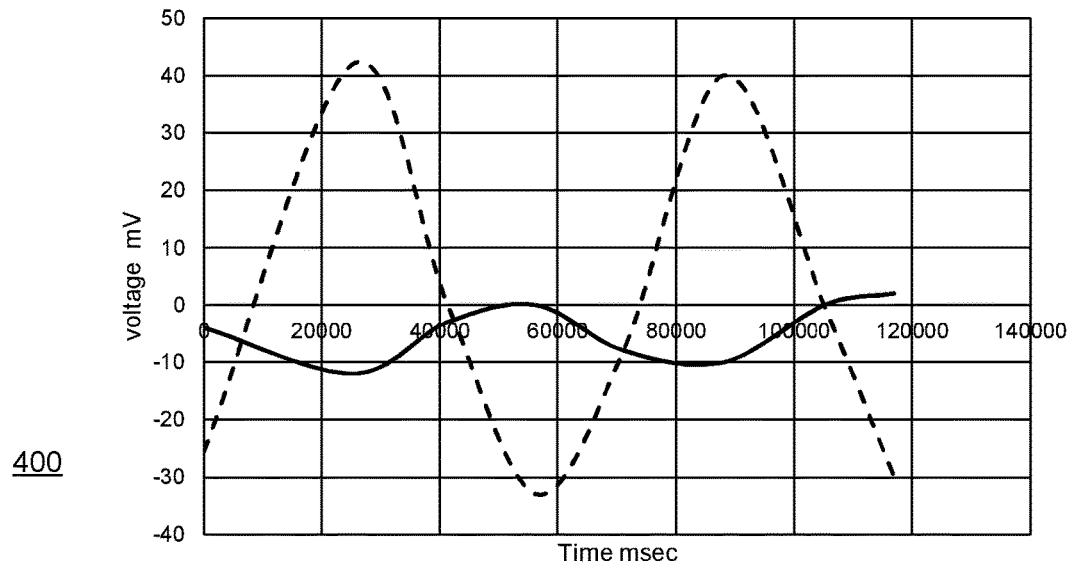
FIG. 4 shows diagram illustrating non-limiting example of the monitoring substance properties according to some embodiments of the present invention.

FIG. 4 shows a graph diagram 400 illustrating non-limiting example of the monitoring substance properties according to some embodiments of the present invention. Graph 400 shows voltage fluctuation over time in a piezoelectric substance indicative of polarization order of the substance. As apparent from graph 400, the polarization of poled substance (dashed line) results in a higher voltage amplitude compared with un-poled substance (same material). These voltage fluctuations can be easily measured by an external apparatus as will be illustrated hereinafter. An in between levels of polarization (or intermediate polarization) may be introduced and predefined such that a unique signature of the voltage over time may indicate the authentication or the usage condition of the article of manufacturing. When preparing in advance a monitoring substance which is configured to undergo a partial polarization to a certain degree a unique voltage behavior may be achieved and very difficult to counterfeit or reproduced without the knowledge of the monitoring substance configuration (mixture ration, spatial location in article, curie point and the like).

Figure 5A:
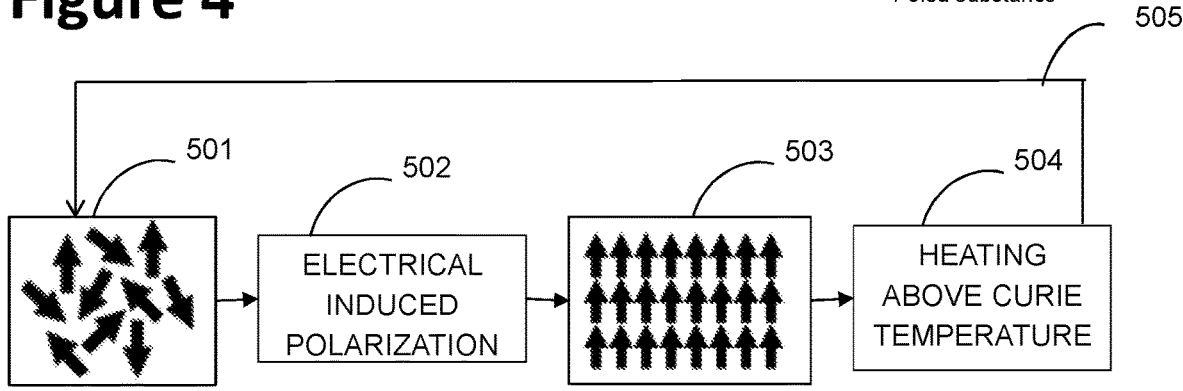
FIG. 5A shows a diagram of a monitoring substance according to some embodiments of the present invention.

FIG. 5A shows a diagram of a monitoring substance according to some embodiments of the present invention. An un-poled substance 501 undergoes electrical induced polarization 502 which results in a poled substance 503. It is then being heated to a Curie temperature 504 resulting in return to un-poled substance as indicated by route 505. Thus, in some embodiments, the change of the at least one physical property of the substance may be indicative of a duration of substance coupled to the article of manufacture being in a second phase (e.g. the duration in after which the article of manufacture has been heated above a Curie temperature). The time duration of being in the second phase may be indicative of the article of manufacture's condition as affected by the second phase. The Poled monitoring substance may be embedded in the article of manufacturing as a monitoring element (e.g. substance) and a voltmeter or other monitoring devices (e.g. detector or detectors) may read the monitoring element and indicate if the monitoring element is in poled or un poled state, the poled state indicates that the article of manufacture was not in use. The Curie point of the monitoring substance will be breached when the article of manufacture is used again (used condition may be defined and set according to article purpose), thus may allow to monitor the article of manufacturing about its usage condition. It is understood that the Curie temperature may be configurable for different manufacturing processes as may needed be.

Figure 5B:
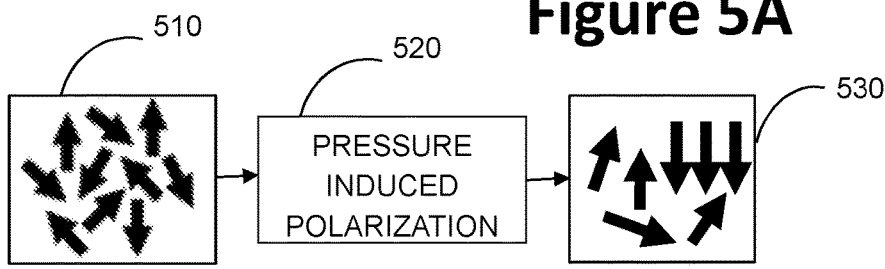
FIG. 5B shows a diagram of a monitoring substance according to some embodiments of the present invention.

FIG. 5B shows a diagram of a monitoring substance according to some embodiments of the present invention. An un-poled substance 510 undergoes pressured induced polarization 520 which results in a partially polarized substance 530. Such partial polarization may be indicative of some pressure related manufacturing, curing, setting, gelation or other physical process that may be measured later and serve as means for determining an authentication or quality of the article of manufacture during a manufacturing process or article life cycle (e.g. determine whether or not an article of manufacture is the result of a predefined known process). The partial polarization may indicate during the life cycle of the article of manufacture if changes to the article properties (such as strength and others) were introduced. In some embodiments, the ferro-elastic substance may be configured to have unique properties after a pressure has been induced thereto.

Figure 6:
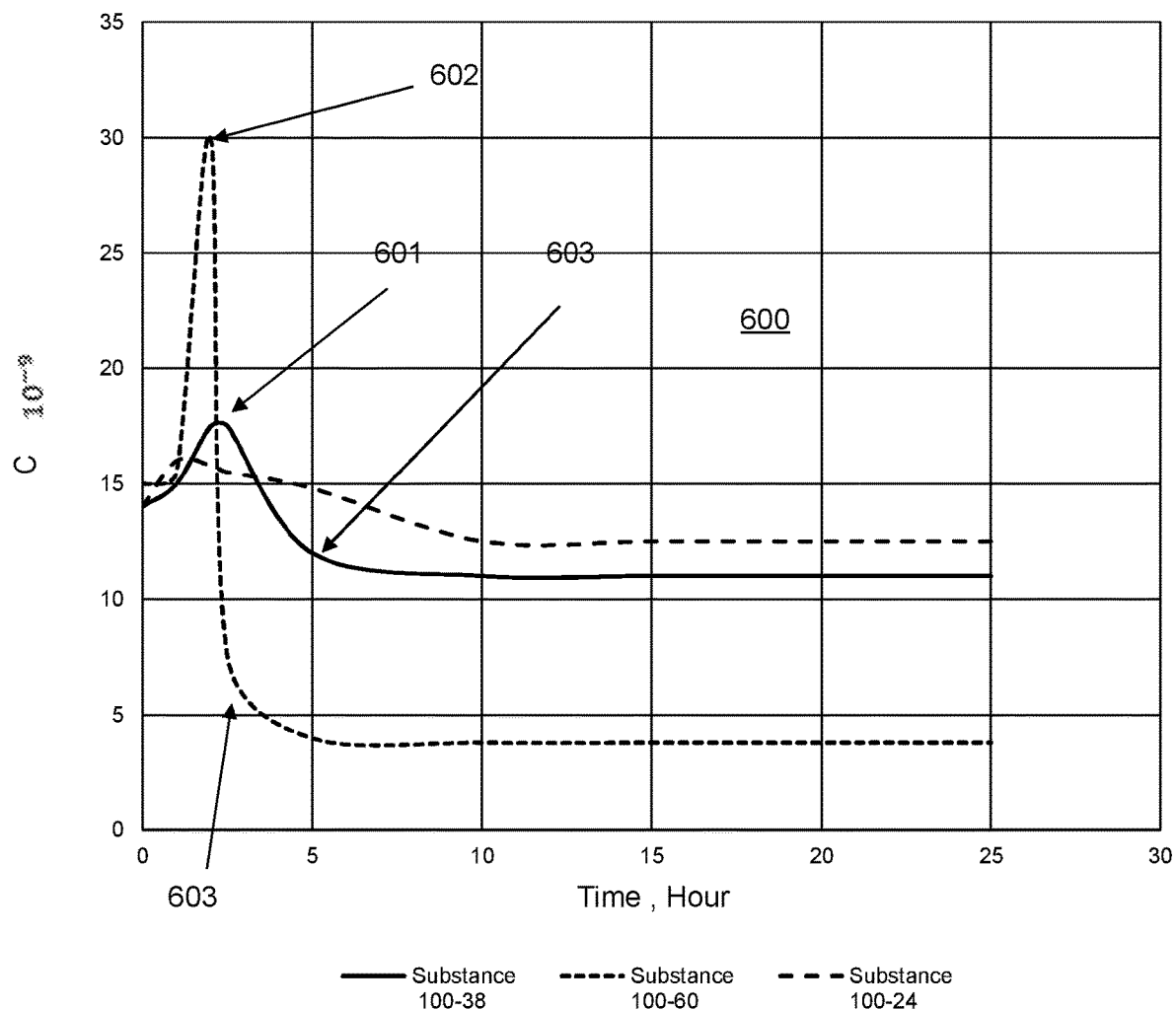
FIG. 6 is a diagram of different monitoring substances behavior over time, in accordance with some embodiments of the present invention.

FIG. 6 is a diagram of different monitoring substances behavior over time, in accordance with some embodiments of the present invention. The monitoring substances are embedded in an article which undergoes curing or setting process which may generate a pressure induced polarization as indicated in FIG. 5B (article may include but not limited to: glue, epoxy, concrete, sealant, soil, asphalt, ink, gel or any other artificial and/or biological substance or compound which is changing during its manufacturing, transportation or storage). Graph 600 illustrates capacitance (by way of example) of a monitoring substance as a function of time during curing process (curing process for example is the process of glue or concrete when setting from liquid to solid). During the curing process the article introduces pressure changes to the monitoring substance (usually increase in pressure) until a steady state is achieved. When adding a monitoring substance such as a ferro-elastic monitoring element during curing process of an article the pressure may generate a pressure induced polarization to the ferro-elastic monitoring substance, a partial or full polarization may occur which may be monitored as capacitance over time (different characteristics of the polarization effect on the monitoring element may be monitored not just capacitance) monitoring the pressure induced polarization on the monitoring substance may indicate manufacturing process parameters such as: authentication, strength, quality, substance mix ratio and more. Thus, any deviation from a predefined manufacturing process may be recorded and detected as a change to the one or more physical properties of the substance attached to the article of manufacture. The monitored change may be evident of a non-authentic manufacture process or a non-compliant product in view of specified quality assurance requirements.

For example, such deviation from a specified manufacturing process may be seen in graph 600 of FIG. 6. An exemplary non-limiting manufacturing parameter (e.g. capacitance) is shown over time in plot line 601 representing substance having a mix ratio of 100-38 whereas a deviation of a predefined threshold from plot line 601 may be seen plot line 602 representing substance having a different mix ratio of 100-60.

When introducing a monitoring substance such as pressure-induced Ferro-elastic monitoring element, different types of graph behavior may indicate different types of articles or different type of manufacturing process, the graphs indicating different points such as point 602 which exhibits the exothermic maximum, point 601 may indicate substance gelation end and point 603 may reflect the gelation start point. This characteristic may be used to determine authenticity, quality, mix ratio strength and other parameters of a substance in a manufacturing process or in different curing procedures (such as applying concrete in a building), by knowing the monitored article, what kind of process it underwent during the manufacturing and compare it to the known process and its effects on the same article may indicate if the process complied with the predefined process and article definitions. In cases of epoxy curing or concrete setting time the required quality of the article final stage may be evaluated based on the final steady state indicated at its beginning in point 603 and thereafter. In different type of articles mixing ratios points 601, 602, 603 and the overall graph behavior may change to indicate either a non-authenticated process or a low quality of article used compared to a good quality article graph. A threshold may be used in order to indicate the allowed deviations from a good quality reference. In case of detecting and monitoring different mix rations in an article of manufacture when analyzing article having mix ratio of 100-38 (solid line), article having mix ratio of 100-60, article having mix ratio of 100-24 and by knowing the behavior and characteristic of each mix ration we may monitor the article by monitoring the capacitance of the monitoring substance graph and report if the mix ratio is not compatible with the required manufacturing process. In another case when a settling time of epoxy or concrete (or other substance) the graph behavior and point 601, 602, 603 may indicate the strength of the article and the overall quality. Parameters such as mix ratio, mix amount, gelation time and others may be controlled and predefined in order to create a unique ID of the process which may indicate on the authenticity of the article and whether it had gone the proper manufacturing process. Using the monitoring ferro-elastic embedded in the article (such as concrete in a building, or epoxy in a chip) may indicate during the life cycle of the article if any changes to the pressure induced polarization on the monitoring substance has occurred, these changes may indicate that the article may experience different changes in strength, moisture, stability, vibrations and other characteristics of the article. The changes may be transmitted to a remote monitoring station which may collect the data and report an alert to the end user. For example, if a monitoring ferro-elastic substance is embedded in different buildings an earth quake may change the steady state of the pressure induced polarization of the monitoring element and thus may indicate according to reading from different places that an earth quake event has occurred.

According to some embodiments of the present invention the ferro-elastic substance may undergo structural phase transition. The structural phase transition may include a pressure induced polarization of the ferro-elastic substance.

According to some embodiments of the present invention the ferro-elastic substance post pressure induced polarization has unique properties that may be used for at least one of: authentication, manufacturing process monitoring, and usage monitoring of said article of manufacture.

According to some embodiments of the present invention the piezo-electric substance comprises ceramic substance.

According to some embodiments of the present invention the at least one physical property comprises a polarity state of the piezo-electric substance.

According to some embodiments of the present invention the polarity state of said piezo-electric substance may be poled in the first phase and un-poled in said second phase.

Figure 7:
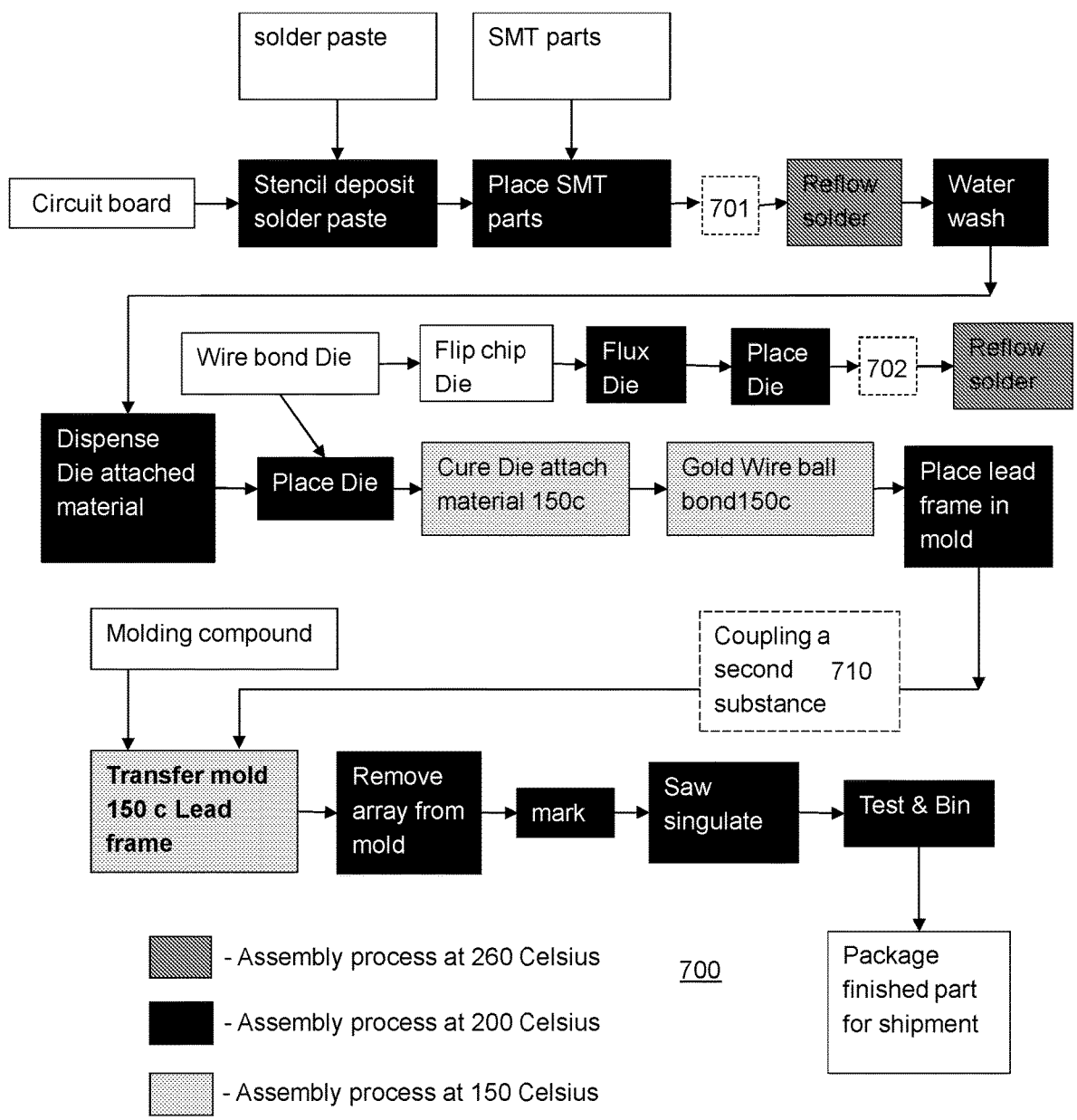
FIG. 7 is a schematic block diagram illustrating coupling of monitoring substance in a manufacturing process, in accordance with some embodiments of the present invention.

FIG. 7 is a schematic block diagram illustrating coupling of monitoring substance in a manufacturing process (may be according to IPC-7093 or any other known standard), in accordance with some embodiments of the present invention. Process 700 is an exemplary non-limiting manufacturing process of a printed circuit board (PCB). As various temperature changes are applied during this process, it is important to locate points along the process that are taking place after all steps beyond the respective Curie temperature have been applied. This point can be point 710 assuming the Curie temperature of the corresponding monitoring material is less than 2600 Celsius and above 200 Celsius. Thus, the monitoring substance remains unchanged (in terms of polarity—remains in poled condition) when it reaches the end of the manufacturing process. Different types of monitoring substances may be applied in different locations in the manufacturing process, by knowing the manufacturing process and the different temperatures applied in different manufacturing locations a monitoring element with a predefined curie point may be introduced in manufacturing process location such as 701 and 702. Location 701 and 702 in this manufacturing process are a step before applying temperature of 2600 Celsius in the manufacturing process. By configuring different types of monitoring substances with different curie point we may apply a monitoring substance configured to undergo phase transition below 2600 Celsius in location 701 and another monitoring substance configured to undergo phase transition above 2600 Celsius in location 702, in this case two monitoring substances will be embedded in the article of manufacture one in poled condition and the other in un-poled, the different combinations and configurations may allow to introduce an ID signature in the process which may be monitored during the life cycle of the IC and may be transmitted to an end user or a monitoring station. Such monitoring combinations and different poled un poled or partially poled condition may be configured to be unique and very hard to reproduce or counterfeit. Placing the monitoring substance in a predefined spatial location in the IC with known polarization configuration, different curie points, different monitoring substance mixture and many other predefined configuration parameters will allow to introduce a unique signature to the article. Using an in between poled transition to the monitoring substance may generate a phase transition which may create a unique pattern known only for the manufacturer.

According to some embodiments of the present invention, physical coupling of the substance to the article of manufacture may be carried out during a process of manufacturing thereof, as a step applied in parallel to said process of manufacturing.

FIG. 8 is an exemplary non-limiting diagram illustrating an architecture of an IC 804 with a monitoring substance 802 attached in accordance with some embodiments of the present invention. Within package IC 801, an IC 804 is connected to a PCB 803 via wire bonds 807. Various soldering points 805, 805A, 805B, 805C, and 805 allow connecting the IC to different ports. A monitoring substance of the type discussed herein is coupled to the PCB in a manner that guarantees its exposure to any change of usage affecting the PCB or the IC. The monitoring substance 802 according to one of the embodiments may be in poled condition and with unique signature of voltage over time (such as indicated in FIG. 4), in this case the monitoring substance may indicate according to the voltage readings if the article of manufacturing (the IC) was reused. Reused of the IC may be a case where the IC is removed from its original package and re assembled on a new PCB in an SMT process, going through another SMT process may apply temperature above monitoring substance curie point (such as indicated in FIG. 7) which may cause the monitoring substance to undergo a phase transition to an un-poled or partially un-poled condition. By monitoring the phase condition of the monitoring substance, a usage condition of the IC may be reported.

According to other embodiments of the present invention, a smart device may monitor the substance attached to the article of manufacture. The smart device may include a detector configured to sense the change in the at least one physical property of said piezo-electric substance by detecting a voltage over time pattern indicative of a polarization state of said piezo-electric substance. In other embodiments, the detector may be configured to sense the change in the at least one physical property of said piezo-electric substance by detecting a deviation beyond a predefined threshold of voltage over time measurements.

Figures 8A, 8B:
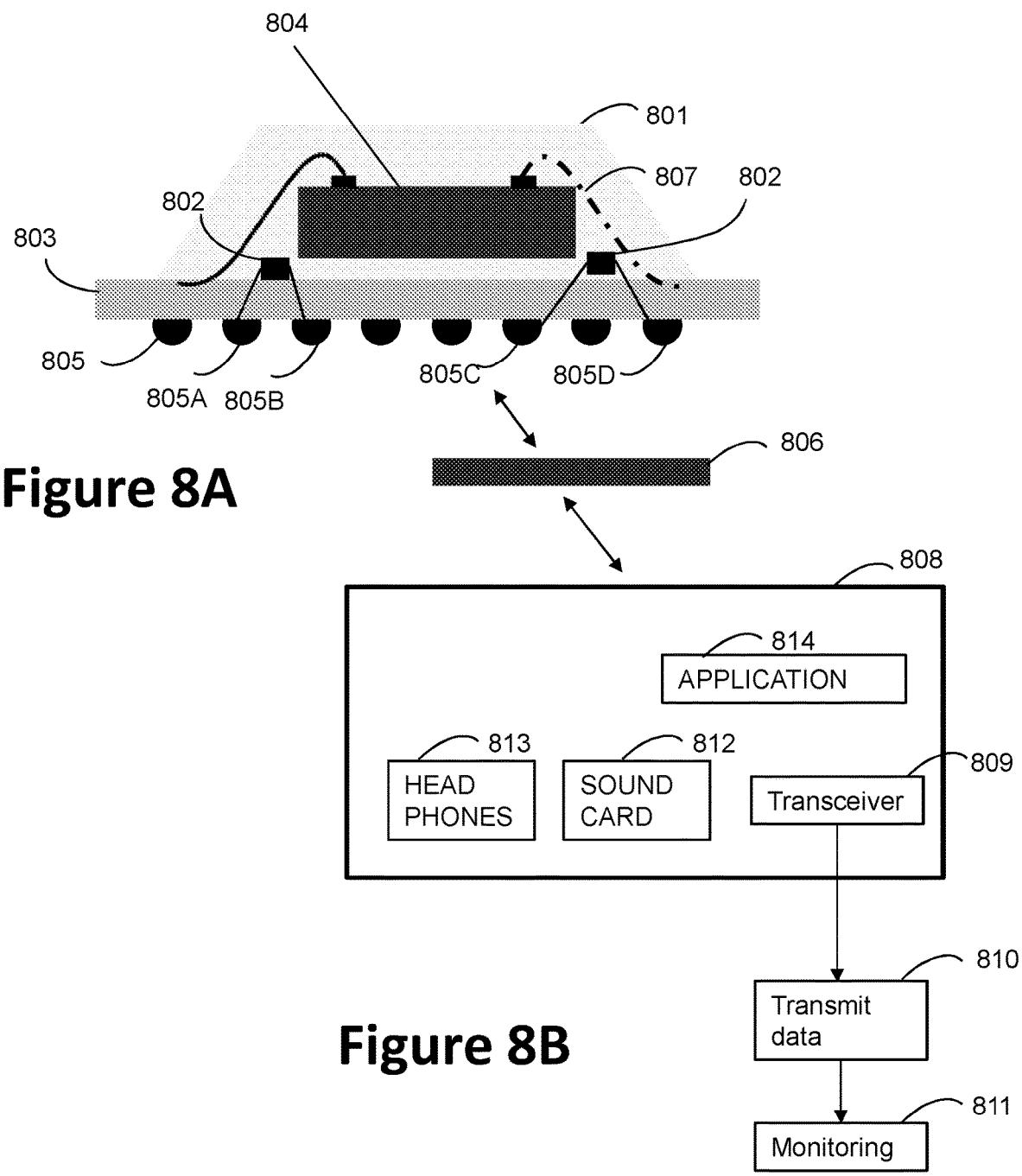
FIG. 8A is a diagram illustrating an architecture of an IC with a monitoring substance in accordance with some embodiments of the present invention.
FIG. 8B is a diagram illustrating a smart device coupled to an article in accordance with some embodiments of the present invention.

FIG. 8B is a diagram illustrating a smart device coupled to an article in accordance with some embodiments of the present invention. The device is configured to sense preferably wirelessly the monitoring substance 802 and deduce, possibly by sensing the polarity or other physical property possibly via an interface such as a port connector 806, whether or not it underwent a use of a predefined type. The device 808 may include a detector operated by an application 814 that determines a use and can either transmits the data via a transceiver 809 where transmitted data 810 are monitored 811 and analyzed (possibly on a cloud) or alternatively this data can be presented as alert via a sound card 812 and headphones 813. The physical condition of the monitoring substance may be transmitted to a monitoring server/station which may contain a database of signatures implemented in each article (IC) and by comparing the analyzed signature and the stored signature may indicate if the article was reused or counterfeited. By comparing a predefined signature of a poled monitoring substance (such as voltage behavior indicated in FIG. 4) to a real reading of the monitoring substance poled condition, the server may detect deviation from the predefined stored signature and may report an alert to the end user or to a monitoring station.

Figure 9:
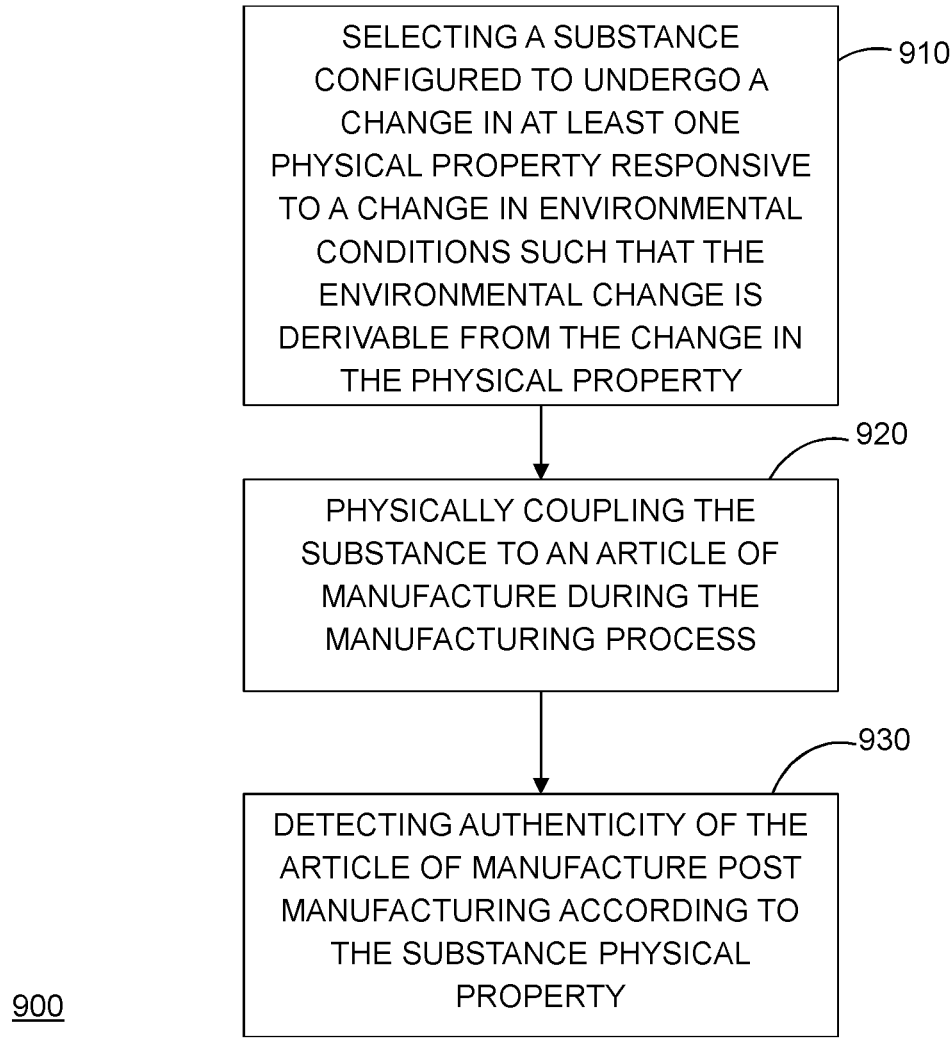
FIG. 9 shows a flowchart diagram of a method using a substance for monitoring an authenticity of article of manufacture according to some embodiments.

FIG. 9 shows a flowchart diagram of a method using a substance for monitoring an authenticity of article of manufacture according to some embodiments. Method 900 may include selecting a substance configured to undergo a change in at least one physical property responsive to a change in environmental conditions such that the environmental change is derivable from the change in the physical property (e.g. the irreversible transition) 910; physically coupling the substance to an article of manufacture prior to the manufacturing process 920; and detecting authenticity of the article of manufacture post manufacturing according to the substance physical property 930.

Figure 10:
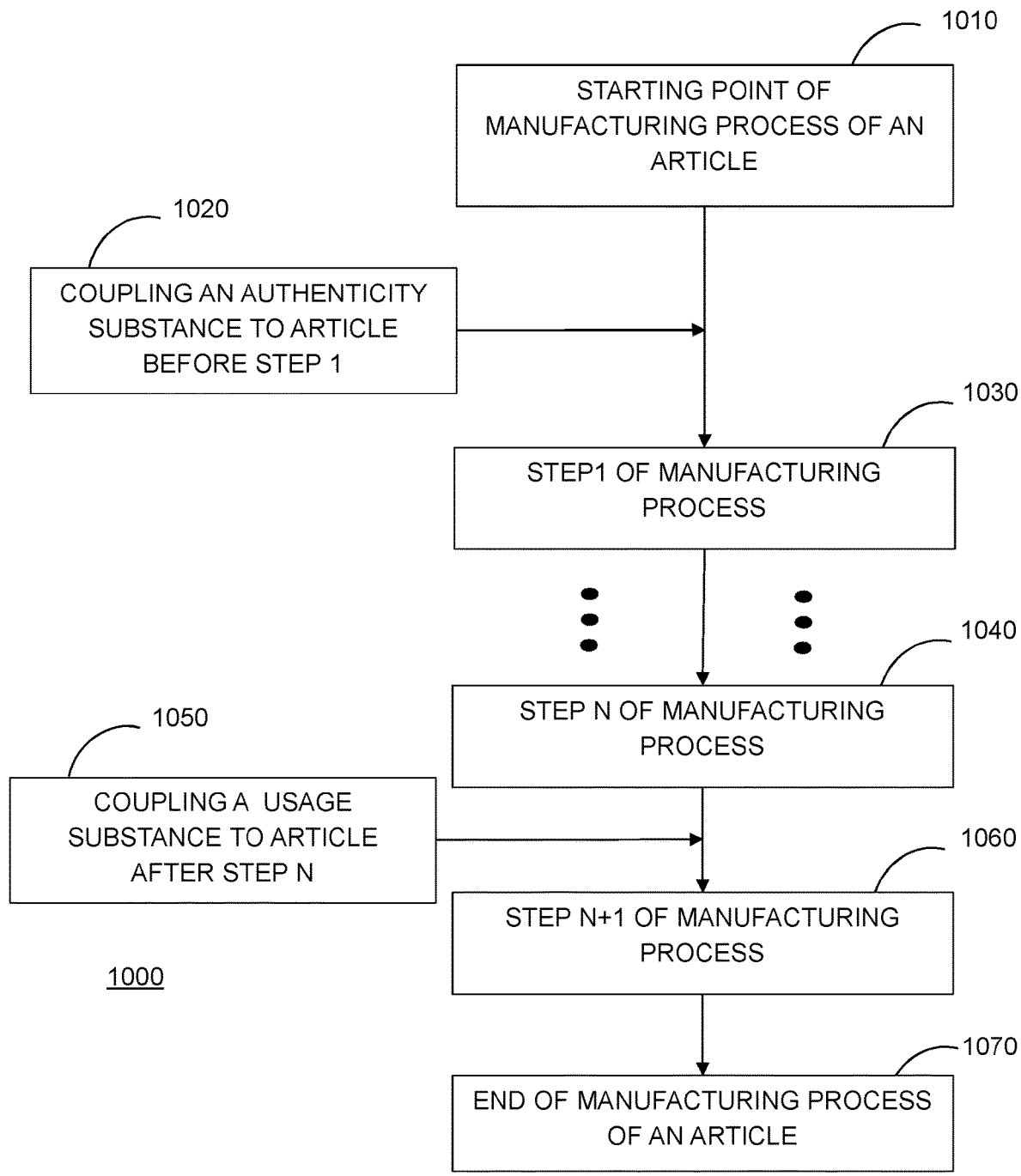
FIG. 10 shows a flowchart diagram of a method for adding both a substance for monitoring an article of manufacture usage condition according to some embodiments.

FIG. 10 shows a flowchart diagram of a method for adding both a substance for monitoring an article of manufacture usage condition according to some embodiments. Any standard manufacturing process may be illustrated by process 1000 which may include starting point of manufacturing process of an article 1010; coupling an authenticity substance to article before step 11020 (e.g. points 701 and 702 in FIG. 7). Then going on to undergo step 1 of manufacturing process 1030. And various steps including step N of manufacturing process 1040. Then, in accordance with some embodiments of the present invention, a step of coupling a substance that serves as a user marker to article before step N+1 1050 is being inserted without interfering with process 1000 which then proceeds to step N+1 of manufacturing process 1060 in other words the coupling should be in a step of the process which do not affect the monitoring substance. Finally, the end of manufacturing process of an article is reached 1070 and any usage or change to the article of manufacture is regarded as post manufacture change that may affect the substance coupled in step 1050 while the authenticity of the article of manufacture can be derived based on substance couple in step 1020.

Figure 11A:
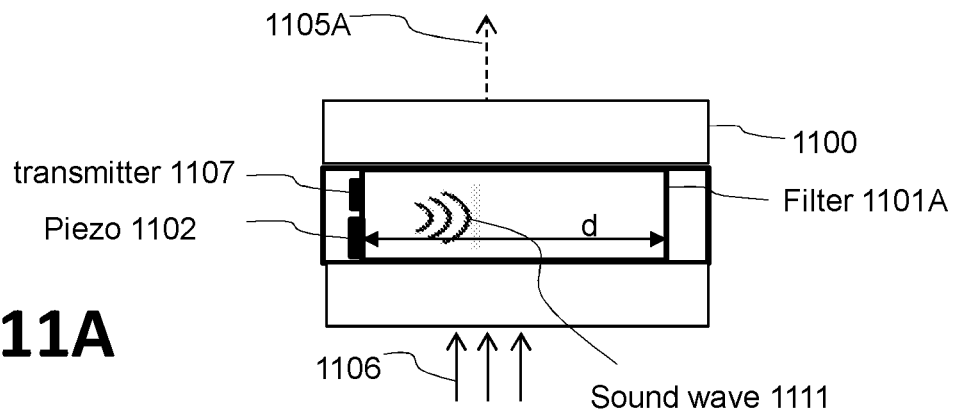
FIG. 11A-11C shows a diagram illustrating an acoustic pulse generator and a sensor device coupled to an article in accordance with some embodiments of the present invention.
Figure 11B:
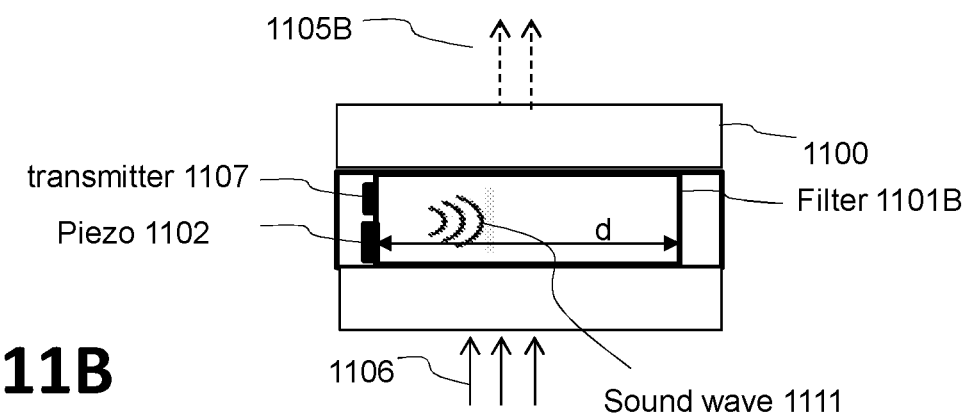
Figure 11C:
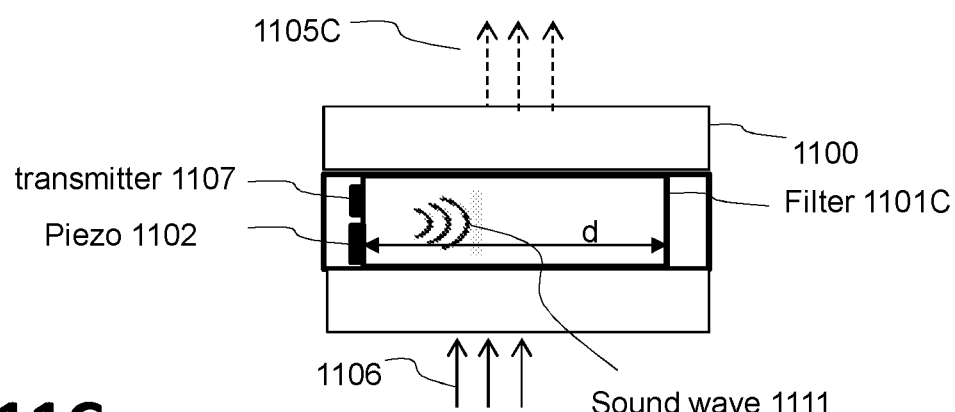

FIGS. 11A-C show yet another embodiment using a monitoring substance 1102 on a filter 1101A-C which may indicate the condition of the filter. The condition of the filter may vary from a starting condition (new filter) 1101A to midlife condition 1101B and final condition 1101C which indicates the filter is not working any more (dead filter). Filter may be any component adapted to absorb some particles and on the other hand to allow other particles to pass (such as oil filter, gas filter, smoke and others). Monitoring substance 1102 may be a piezo-electric monitoring element is placed or coupled to the filter 1102, transmitter 1107 is placed or coupled to filter 1102 either on the same side of the monitoring substance or could be place on the other side of the filter. Transmitter 1107 may generate a sound wave 1111 which according to its velocity may generate a voltage fluctuation on the piezo-electric monitoring substance. In closed environment the velocity of the sound wave would have been remain constant according to equation (2) the distance d remains constant and the sound wave parameters may be controlled thus the time to travel the same distance remains the same and so is the sound wave velocity. In case of a filter acting as a medium which conveys the sound wave a constant distance d, the filter acts as a medium for the sound wave may change its density and may cause the sound wave to travel at different velocity, as indicated in equation (1) module young E of the filter medium does not change but its density may increase as the filter keeps absorbing particles during its working life cycle. Measuring the voltage received in the piezo-electric 1102 monitoring substance indicates that a linkage between the velocity of a sound wave traveling between two side walls of the filter, using equation 1 where E module young is known and depends on the material, the velocity of the sound wave will change according to the density of the material inside the filter, The density of the material inside the filter is changing during the life cycle of the filter, during the use of the filter some of the particles (such as oil) are absorbed in the filter and may change the filter density. The changes in the density will be translated to reading in the piezo-electric sensor placed on the filter wall.

The initial process may start with a calibration step, the calibration step (detailed in FIG. 15) may take different reading of known filters in different conditions such as (but not limited to): first filter in a new condition (not used), a second filter in midlife condition, a third filter in its final condition (dead filter). Transmitting a sound wave 1111 with known parameters and reading in each type of filter the voltage fluctuation over time may indicate the expected readings (FIG. 13) of the filter in each life cycle condition and may be represented in look up table (LUT) such as LUT in FIG. 12.

FIG. 11A shows filter 1101A in a first condition (new filter) situated or coupled to enclosure 1100 which may allow fluid, gas or other working substances to flow through it, working substance direction of flow is indicated 1106 as an inlet and 1105A as the outlet, the number of arrows at 1105A (three arrows in 1106 and one arrow our at 1106A) indicates that the filter is working properly and absorbing a good amount of the particles needed to be filtered. Transmitter 1107 generates a sound wave with known properties which travels inside filter 1101A in a certain velocity which is typical to a specific filter in a first condition (new filter). Piezo-electric monitoring substance generates voltage reading which may correspond to filter condition. Using a wireless transmitter (not shown) coupled to the monitoring substance may allow to transmit piezo-electric readings and the corresponding filter condition to remote monitoring station or user.

Figure 13:
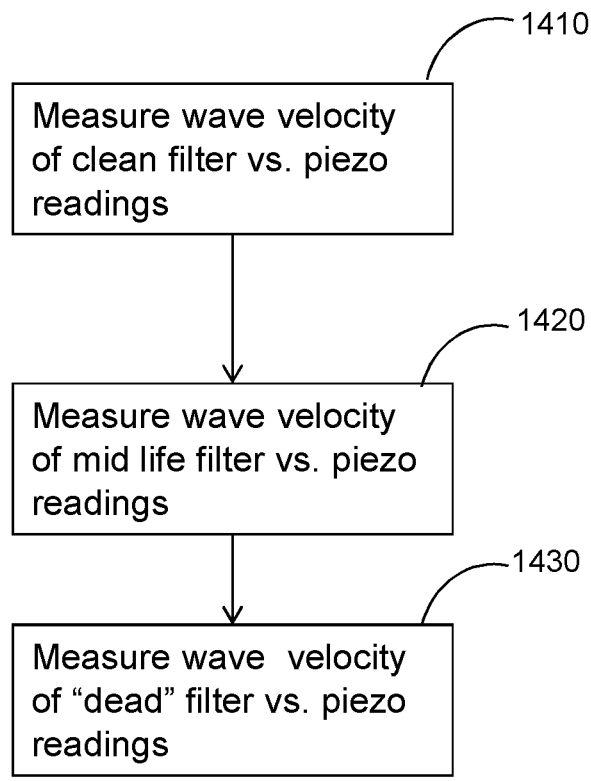
FIG. 13 shows diagram illustrating non-limiting example of the monitoring substance properties according to some embodiments of the present invention.

FIGS. 11B and 11C are the same configuration showing the filter in different life condition, FIG. 11B indicates a midlife filter condition where FIG. 11C shows a filter in the end life where outlet 1105C shows that almost no absorption is done in the filter. In this case the piezo-electric monitoring element will reach a steady state reading such as indicated in FIG. 13, point number 4. By transmitting the filter status to a remote location/user a new filter may be replaced instead of the old filter.

FIGS. 11A-C indicate two piezo-electric sensors placed on the filter walls sides where formula (1) below illustrate the sound wave velocity relationship that corresponds with the operation of these sensors:

$$V_E = \sqrt{\frac{E}{\rho}} \quad (1)$$

Wherein:
ρ density
K bulk modulus=1/compressibility
μ shear modulus
λ Lame's coefficient
E Young's modulus
ν Poisson's ratio
M P-wave modulus=K+(4/3) μ
d=distance between the filters wall, the distance the sound wave needs to travel
t=the time that took to the sound wave to reach the sensing element (piezo) using a standard timing device in equation (2) below:

$$V = \frac{d}{t} \quad (2)$$

Figure 12:
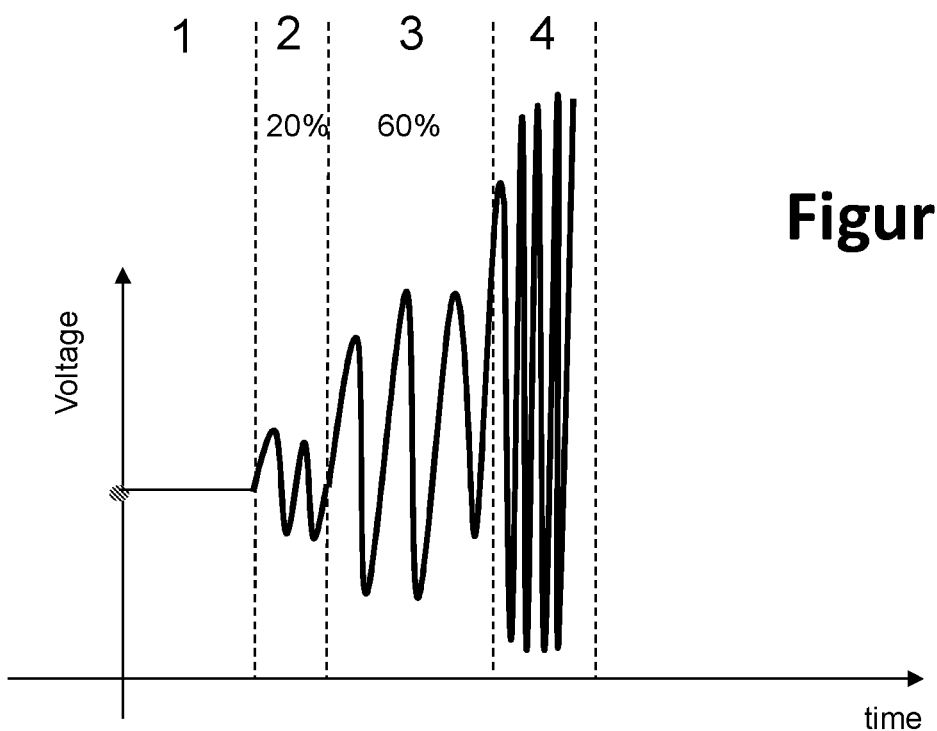
FIG. 12 shows diagram illustrating non-limiting example of the monitoring substance properties according to some embodiments of the present invention.

FIG. 12 illustrates according to another embodiment of the invention a look up table (LUT) prepared in calibration phase, the calibration or learning phase is done a priory to learn the filter (or the article of manufacture) behavior under different usage condition and life cycle.

As one can see the LUT indicates that a "new" filter will read using a piezo sensor such as indicated in FIGS. 11 and 14.

FIGS. 14A-C illustrate non-limiting examples of the monitoring substance properties according to some embodiments of the present invention. FIG. 14A depicts a filter in a first condition (new) consisting of a transmitter and receiver. FIG. 14B is in the same configuration as 14A, depicting the filter a different condition, later in its life (used), again consisting of a transmitter and receiver. FIG. 14C depicts the change in signal between the two transmitters (new and used), wherein the new transmitter is in a dry condition and the used transmitter is in a wet condition.

Figure 15:
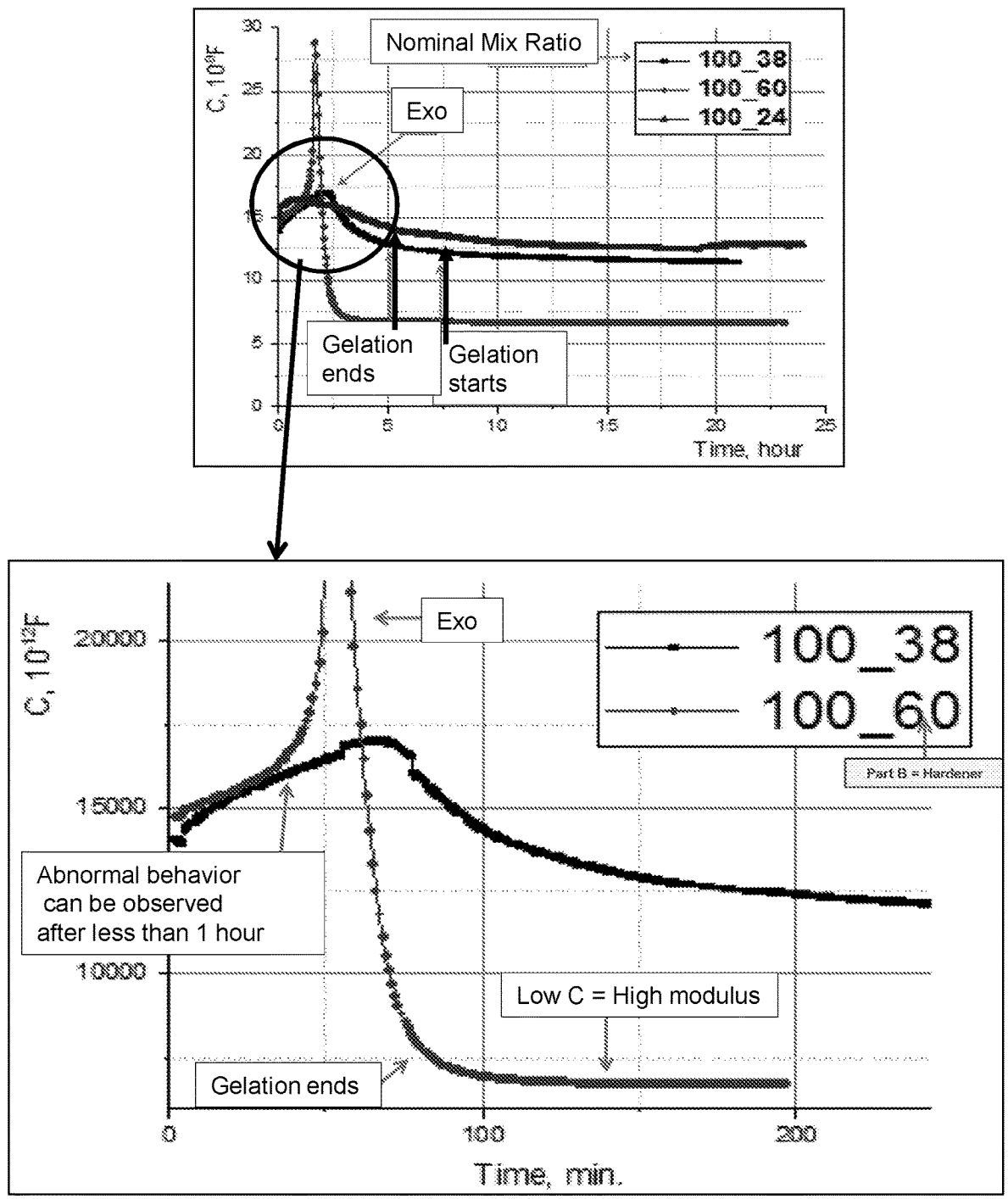
FIG. 15 shows experiment results illustrating non-limiting example of the monitoring substance properties according to some embodiments of the present invention.

FIG. 15 illustrates a graph wherein the changing behavior of substances with differing nominal mix ratios can be observed. The start and end of gelation periods are clearly marked, alongside periods of abnormal behavior and regions at which the substances may harden.

Figure 16:
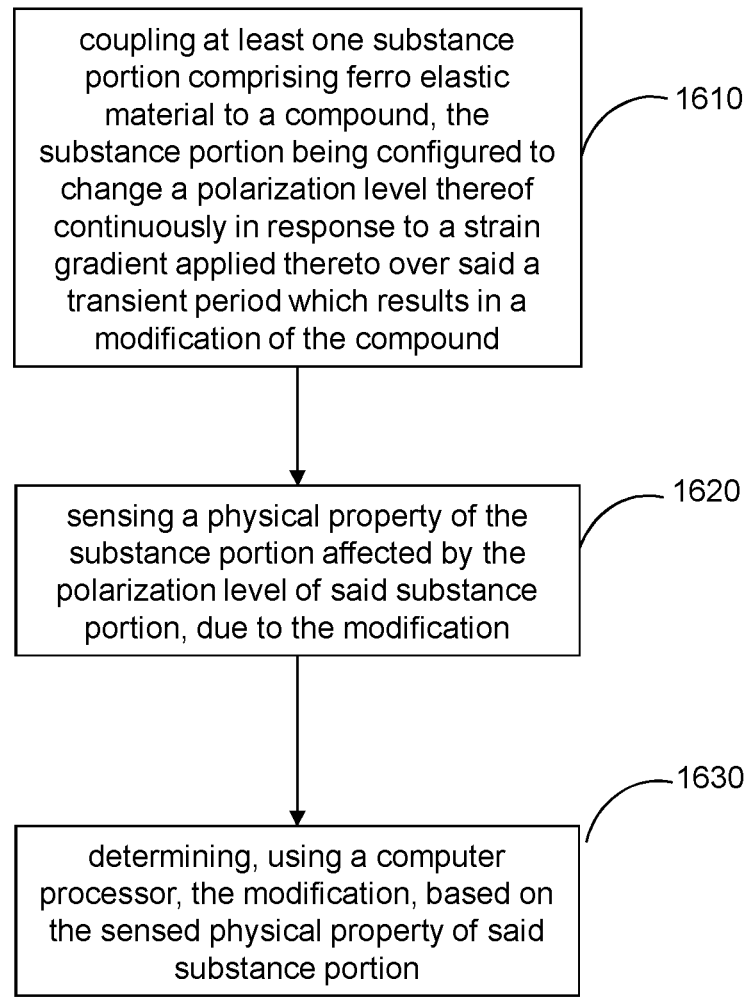
FIG. 16 shows a flowchart diagram of a method for detecting a modification of a compound during a transient period according to some embodiments.

FIG. 16 shows a flowchart diagram of a method for detecting a modification of a compound, said modification occurring during a transient period. Method 1600 may include the following steps: coupling at least one substance portion comprising ferro elastic material to a compound, said substance portion being configured to change a polarization level thereof continuously in response to a strain gradient applied thereto over said a transient period which results in said modification 1610; sensing a physical property of said substance portion affected by the polarization level of said substance portion, due to said modification 1620; and determining, using a computer processor, said modification, based on the sensed physical property of said substance portion 1630.

According to some embodiments of the present invention, the transient period may be a time in which said compound changes from one state to another state or it may be a time in which said compound undergoes solidifying. The transient period is simply the time over which there is a noticeable and detectable change in the compound.

According to some embodiments, the modification may be a different metric per the compound under test. In a case that the compound is concrete, the modification metric may be compression strength (e.g. standard ASTM C39). For glues, the respective modification metric would be glass transition temperature.

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the reminder of the description the term "detector" or "detectors" may relate to the aforementioned ferro-elastic substance portions configured to undergo a pressure-induced polarization, that may be later sensed and used to monitor the modification to the compound to which they are coupled.

Figure 17:
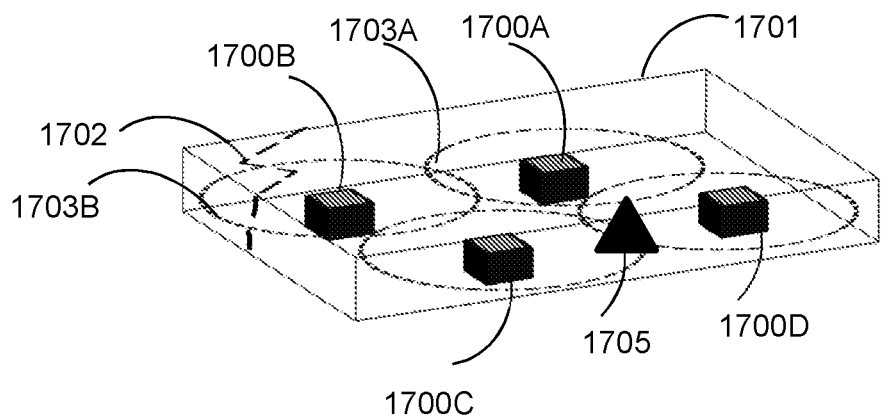
FIG. 17 is a diagram illustrating a possible arrangement in accordance with some embodiments of the present invention.

FIG. 17 is a diagram illustrating a possible arrangement in accordance with some embodiments of the present invention. In this arrangement, an array of detectors 1700A-1700D made of the ferro-elastic substance portions are coupled or embedded within compound 1701 and each can be sensed as explained above to determine modification and strain within compound 1701 in the transient period and also in the steady state period after the transient period ended. Thus, a crack such as 1702 occurring during transient period or the steady state may affect the pressure or strain and based on the difference in level of strain measured by the detectors may be detected. Similarly, using triangulation based on the respective radii surrounding the detectors (such as 1703B or 1703A) an event 1705 that affects strain gradient may be detected and located. The event may occur either during the transient period or in the steady state.

Figure 18:
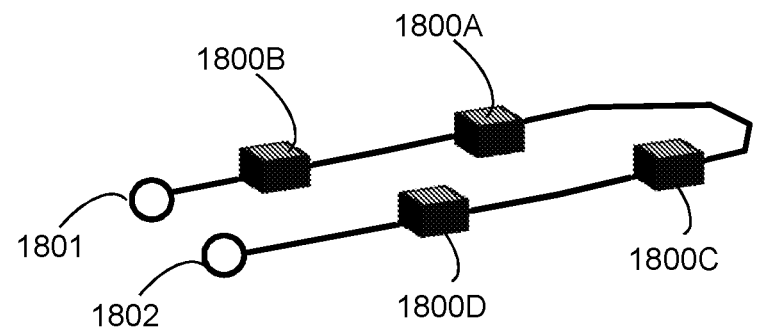
FIG. 18 is a diagram illustrating a possible arrangement in accordance with some embodiments of the present invention.

FIG. 18 is a diagram illustrating a possible arrangement in accordance with some embodiments of the present invention. In this arrangement, several detectors 1800A-1800D are connected in series and over a cable with two nodes 1801 and 1802 that can be connected to a network. The connection in series is advantageous in using minimal wiring and easy deployment. It is also advantageous as all detectors share the same communication and power wiring. Point 1802 can be located in a secure position not affected by the concrete and can be thus easily connected to other networks without interference. Additionally, it can be used for getting a good averaging of the strain gradient within the compound under test.

Figure 19:
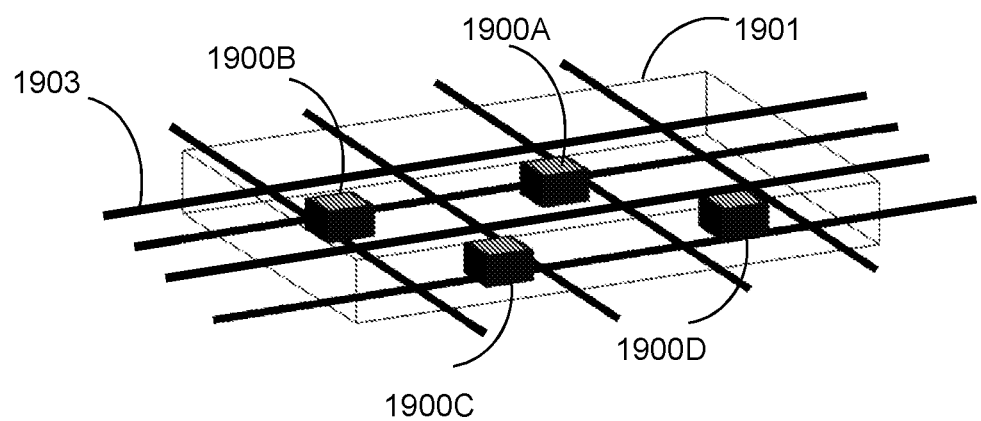
FIG. 19 is a diagram illustrating a possible arrangement in accordance with some embodiments of the present invention.

FIG. 19 is a diagram illustrating a possible arrangement in accordance with some embodiments of the present invention. In this arrangement possibly an already existing grid of metal 1903 (used for structural reasons) embedded within the compound under test 1901 (e.g. concrete) serves as a wiring network of the array of detectors of ferro-elastic substance 1900A-1900D. This arrangement of parallel wiring is advantageous in allowing a better localization of strain-related events occurring during steady state phase. This is since each detector can be monitored individually. Additionally, the metal grid may serve as infrastructure for delivering power and communication for the array of detectors.

Figure 20:
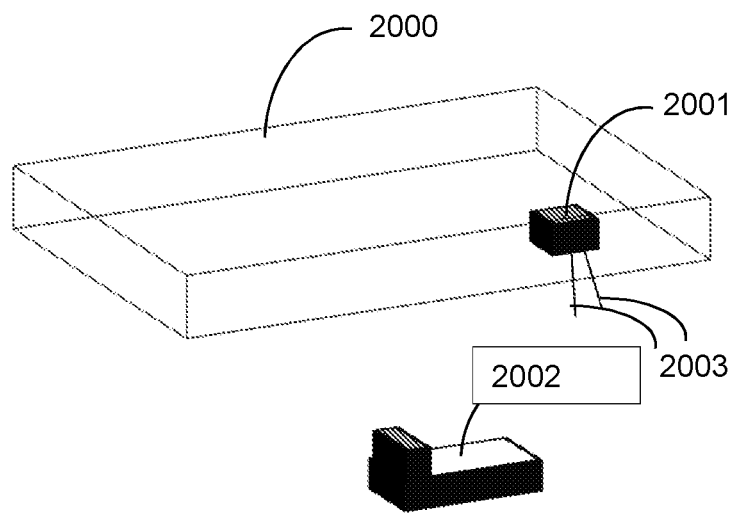
FIG. 20 is a diagram illustrating a possible arrangement in accordance with some embodiments of the present invention.

FIG. 20 is a diagram illustrating a possible arrangement in accordance with some embodiments of the present invention. In this arrangement a smartphone 2002 or any device with wireless connectivity (e.g. dedicated sensing device, possibly installed on drones) may be used to sense levels of strain gradient within compound 2000 as applied to ferro-elastic detector 2001 which is provided with wireless connectivity. Alternatively, monitoring is carried out via pins 2003. Alternatively, the communication with detector 2001 may be carried out via near field communication (NFC).

Figure 21:
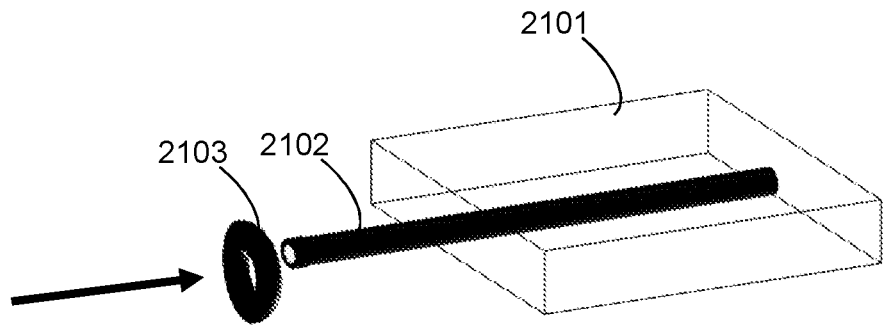
FIG. 21 is a diagram illustrating a possible arrangement in accordance with some embodiments of the present invention.

FIG. 21 is a diagram illustrating a possible arrangement in accordance with some embodiments of the present invention. In this arrangement it is shown how a detector embedded within a ring (such as a rubber ring 2103) may be easily attached to a structural metal rod 2102 used for structural reasons in a concrete block 2101. This embodiment is a retro-fit arrangement that is using existing infrastructure (metal grid) for stabilizing and possibly wiring the detector to a network.

Figure 22:
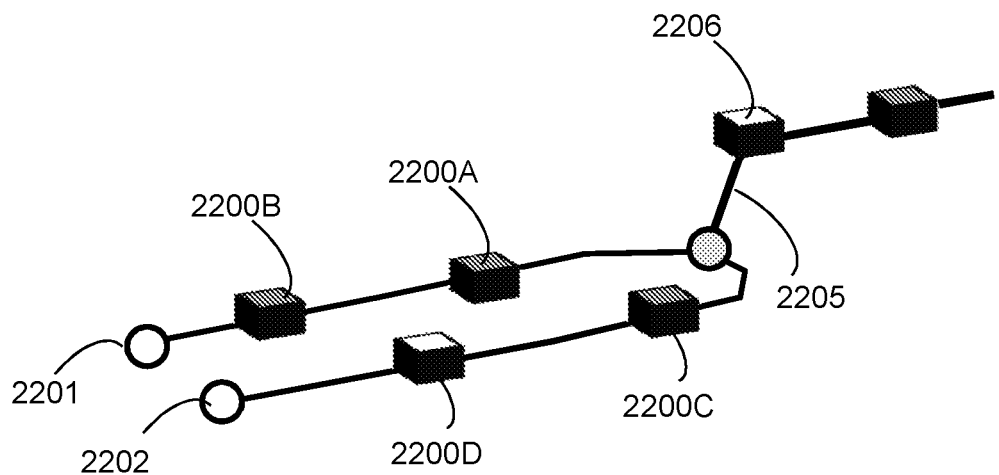
FIG. 22 is a diagram illustrating a possible arrangement in accordance with some embodiments of the present invention.

FIG. 22 is a diagram illustrating a possible arrangement in accordance with some embodiments of the present invention. This arrangement shows how several detectors 2200A-2200D can be deployed in an ad hoc network in which super node 2200D can collect readings from ordinary nodes 2200A, 2200B and 2200C and convey it to another network 2205 and possibly super node 2206 and from there to further networks via further super nodes. Advantageously this arrangement contributes to scalability of the present invention.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions. It will further be recognized that the aspects of the invention described hereinabove may be combined or otherwise coexist in embodiments of the invention.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" substance, that does not preclude there being more than one of the additional substance.

It is to be understood that where the claims or specification refer to "a" or "an" substance, such reference is not be construed that there is only one of that substance.

It is to be understood that where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention.

The invention claimed is:

1. An apparatus for detecting a modification of a compound, said modification occurring during a transient period, comprising:
    at least one substance portion comprising ferro elastic material coupled to said compound and configured to change a polarization level thereof continuously in response to a strain gradient applied thereto over said transient period;
    a sensor configured to sense a physical property of said substance portion affected by the polarization level of said substance portion, due to said modification; and a computer processor configured to determine said modification, based on the sensed physical property of said substance portion, wherein said computer processor is configured to determine a modification of the compound based on a table mapping levels of changes to the physical property of the substance portion and levels of modifications of the compound.

2. The apparatus according to claim 1, wherein the transient period is a time in which said compound changes from one state to another state.

3. The apparatus according to claim 1, wherein the transient period is a time in which said compound undergoes solidifying.

4. The apparatus according to claim 1, wherein said compound is glue or concrete.

5. The apparatus according to claim 1, wherein a change in the at least one physical property is predicted using a local sensing element to sense local weather conditions in combination with a pre-existing historical database.

6. An apparatus for detecting a modification of a compound, said modification occurring during a transient period, comprising:

at least one substance portion comprising ferro elastic material coupled to said compound and configured to change a polarization level thereof continuously in response to a strain gradient applied thereto over said transient period;

a sensor configured to sense a physical property of said substance portion affected by the polarization level of said substance portion, due to said modification; and a computer processor configured to determine said modification, based on the sensed physical property of said substance portion, wherein said at least one substance portion comprises a plurality of substance portions embedded in different locations within said compound, wherein said computer processor is further configured to determine modification of the compound during said transient period, based on the sensed physical property of said plurality of substance portions.

7. The apparatus according to claim 6, wherein said computer processor is further configured to determine a three-dimensional modification of said compound during the transient period.

8. The apparatus according to claim 6, further comprising a wireless rechargeable power supply and at least one detector, wherein the at least one detector is charged via radio frequency electromagnetic waves.

9. An apparatus for detecting a modification of a compound, said modification occurring during a transient period, comprising:

at least one substance portion comprising ferro elastic material coupled to said compound and configured to change a polarization level thereof continuously in response to a strain gradient applied thereto over said transient period;

a sensor configured to sense a physical property of said substance portion affected by the polarization level of said substance portion, due to said modification;

a computer processor configured to determine said modification, based on the sensed physical property of said substance portion; and a sensor module consisting of a processor and a data transmission module for transmitting data to a main hub or smart box.

10. The apparatus according to claim 9, further comprising one or more secondary hubs that receive data from sensors and transmit and to the main hub, wherein the main hub transmits the data to the internet.

11. A method for detecting a modification of a compound, said modification occurring during a transient period, said method comprising:

coupling at least one substance portion comprising ferro elastic material to a compound, said substance portion being configured to change a polarization level thereof continuously in response to a strain gradient applied thereto over said transient period which results in said modification;

sensing a physical property of said substance portion affected by the polarization level of said substance portion, due to said modification; and determining, using a computer processor, said modification, based on the sensed physical property of said substance portion, wherein the transient period is a time in which said compound changes from one state to another state.

12. The method according to claim 11, wherein the transient period is a time in which said compound undergoes solidifying.

13. The method according to claim 11, wherein said compound is glue or concrete.

14. The method according to claim 11, further comprising determining a modification of the compound based on a table mapping levels of changes to the physical property of the substance portion and levels of modifications of the compound.

15. The method according to claim 11, wherein said at least one substance portion comprises a plurality of substance portions embedded in different locations within said compound, wherein said computer processor is further configured to determine modification of the compound during said transient period, based on the sensed physical property of said plurality of substance portions.

16. The method according to claim 15, further comprising determining a three-dimensional modification of said compound during the transient period.

17. The method according to claim 11, wherein said change in the at least one physical property is predicted using a local sensing element to sense local weather conditions in combination with a pre-existing historical database.

18. The method according to claim 11, further comprising transmitting data to a main hub or smart box.

* * * * *